US012256952B2

(12) United States Patent
Jiménez González et al.

(10) Patent No.: US 12,256,952 B2
(45) Date of Patent: Mar. 25, 2025

(54) SYSTEM FOR THE CONTROLLED FRAGMENTATION OF SOLIDS BY MEANS OF VORTEX SOUND BEAMS

(71) Applicants: UNIVERSITAT POLITÈCNICA DE VALÈNCIA, Valencia (ES); CONSEJO SUPERIOR DE INVESTIGACIONES CIENTÍFICAS (CSIC), Madrid (ES)

(72) Inventors: Noé Jiménez González, Valencia (ES); Francisco Camarena Femenia, Valencia (ES); Jose María Benlloch Baviera, Valencia (ES)

(73) Assignees: UNIVERSITAT POLITÈCNICA DE VALÈNCIA, Valencia (ES); CONSEJO SUPERIOR DE INVESTIGACIONES CIENTÍFICAS (CSIC), Madrid (ES)

(*) Notice: Subject to any disclaimer, the term of this patent is extended or adjusted under 35 U.S.C. 154(b) by 163 days.

(21) Appl. No.: 18/017,004

(22) PCT Filed: Jul. 15, 2021

(86) PCT No.: PCT/ES2021/070524
§ 371 (c)(1),
(2) Date: Jan. 19, 2023

(87) PCT Pub. No.: WO2022/018311
PCT Pub. Date: Jan. 27, 2022

(65) Prior Publication Data
US 2023/0346407 A1 Nov. 2, 2023

(30) Foreign Application Priority Data
Jul. 20, 2020 (ES) ................ ES202030757

(51) Int. Cl.
*A61B 17/225* (2006.01)
*B06B 1/02* (2006.01)
(Continued)

(52) U.S. Cl.
CPC ...... *A61B 17/2255* (2013.01); *A61B 17/2256* (2013.01); *B06B 1/0215* (2013.01); *B06B 1/0607* (2013.01); *A61B 2017/0011* (2013.01)

(58) Field of Classification Search
CPC ........... A61B 17/2255; A61B 17/2256; A61B 2017/0011; A61B 2017/22028;
(Continued)

(56) References Cited

U.S. PATENT DOCUMENTS 4,865,042 A * 9/1989 Umemura ............ G10K 11/346
310/334
4,928,672 A * 5/1990 Grasser .............. A61B 17/2258
601/4
(Continued)

FOREIGN PATENT DOCUMENTS

WO   20010180708 A2   11/2001
WO   2004089188 A2   10/2004
WO   WO 2004089188   *   5/2005

OTHER PUBLICATIONS

W. Folberth et al., "Pressure distribution and energy flow in the focal region of two different electromagnetic shock wave sources", J. Stone Dis., 1992, vol. 4, Issue 1, pp. 1-7.
(Continued)

*Primary Examiner* — Alexei Bykhovski
(74) *Attorney, Agent, or Firm* — Hayes Soloway P.C.

(57) ABSTRACT

The present invention relates to a system for the controlled fragmentation of solids by means of acoustic beams, comprising at least one acoustic beam generation unit (100); and one feedback and control unit (200) of said generation unit
(Continued)

(100). Advantageously, the acoustic beams generated by the system are acoustic vortex beams; and the feedback and control unit (200) further comprises a feedback subsystem (12), configured to receive the information relating to the fragmented solids and to utilize it so as to adapt the operation of the acoustic beam generation unit (100). Given that the generation of shearing stresses is more efficient using vortex beams, the amplitudes of the ultrasonic field needed to fragment the calculi are much lower than in current extracorporeal shock wave lithotripsy techniques. Likewise, the system minimizes unwanted effects on soft tissues surrounding the solid.

15 Claims, 13 Drawing Sheets

(51) Int. Cl.
*B06B 1/06* (2006.01)
*A61B 17/00* (2006.01)

(58) Field of Classification Search
CPC . A61B 17/2258; A61B 17/225; B06B 1/0215; B06B 1/0607
See application file for complete search history.

(56) References Cited

U.S. PATENT DOCUMENTS

| | | | | |
|---|---|---|---|---|
| 4,957,099 | A | * | 9/1990 | Hassler ............ G10K 11/355 601/4 |
| 5,209,222 | A | | 5/1993 | Viebach |

OTHER PUBLICATIONS

Jimenez et al., "Sharp acoustic vortex focusing by Fresnel-spiral zone plates," AIP Publishing, Applied Physics Letters, 2018, vol. 112, Issue 20, p. 204101, 6 pages.
Cleveland et al., "Effect of stone motion on in vitro comminution efficiency of Storz Modulith SLX", PubMed, National Library of Medicine, J. Endourol., 2004, vol. 18, Issue 7, pp. 629-633, 6 pages.
Kim et al., "Cystine calculi: Correlation of CT-visible structure, CT number, and stone morphology with fragmentation by shock wave lithotripsy", SpringerLink, Urological Research, 2007, vol. 35, Issue 6, pp. 319-324, 6 pages.
D. L. Sokolov et al., "Dual-pulse lithotripter accelerates stone fragmentation and reduces cell lysis in vitro," PubMed, National Library of Medicine, Ultrasound Med. Biol., 2003, vol. 29, Issue 7, pp. 1045-1052, 8 pages.
C. Chaussy et al., "Extracorporeally Induced Destruction of Kidney Stones by Shock Waves", PubMed, National Library of Medicine, Lancet, 1980, vol. 2, Issue 8207, pp. 1265-1268, 4 pages.
C. Bohris et al., "Hit/miss monitoring of ESWL by spectral Doppler ultrasound", Elsevier, Ultrasound Med. Biol., 2003, vol. 29, Issue 5, pp. 705-712, 8 pages.
X. Xi and P. Zhong, "Improvement of stone fragmentation during shock-wave lithotripsy using a combined EH/PEAA shock-wave generator-in vitro experiments," Elsevier, Ultrasound Med. Biol., 2000, vol. 26, Issue 3, pp. 457-467, 11 pages.
A. P. Evan et al., "Independent assessment of a wide-focus, low-pressure electromagnetic lithotripter: absence of renal bioeffects in the pig", Journal Compilation, BJU Int, 2008, vol. 101, Issue 3, pp. 382-388, 7 pages.
J. A. McAteer et al., "Independent Evaluation of the Lithogold LG-380 Lithotripter: In Vitro Acoustic Characteristics and Assessment of Renal Injury in the Pig Model", The Journal of Urology, 2009, vol. 181, Issue 4, pp. 665-666, 2 pages.
R. O. Cleveland and O. A. Sapozhnikov, "Modeling elastic wave propagation in kidney stones with application to shock wave lithotripsy", J. Acoust. Soc. Am., 2005, vol. 118, Issue 4, pp. 2667-2676, 10 pages.
K. Maeda et al., "Energy shielding by cavitation bubble clouds in burst wave lithotripsy," J. Acoust. Soc. Am., 2018, vol. 144, Issue 5, pp. 2952-2961, 10 pages.
T. G. Leighton and R. O. Cleveland, "Lithotripsy", Proc. Inst. Mech. Eng. Part H J. Eng. Med., 2010, vol. 224, Issue 2, pp. 317-342, 26 pages.
A. Z. Weizer et al., "New Concepts in Shock Wave Lithotripsy," Elsevier, Urol. Clin. North Am., 2007, vol. 34, Issue 3, pp. 375-382, 8 pages.
Y. A. Pishchalnikov et al, "Air Pockets Trapped During Routine Coupling in Dry Head Lithotripsy Can Significantly Decrease the Delivery of Shock Wave Energy," J. Urol., 2006, vol. 176, Issue 6, pp. 2706-2710, 11.
J. J. Rassweiler et al., "Shock Wave Technology and Application: An Update", Eur. Urol., 2011, vol. 59, Issue 5, pp. 784-796, 23 pages.
L. J. Wang et al., "Predictions of outcomes of renal stones after extracorporeal shock wave lithotripsy from stone characteristics determined by unenhanced helical computed tomography: A multivariate analysis", Eur. Radiol, 2005, vol. 15, Issue 11, pp. 2238-2243, 6 pages.
W. Folberth et al., "Pressure distribution and energy flow in the focal region of two different electromagnetic shock wave sources", J. Stone Dis., 1992, vol. 4, Issue 1, pp. 1-7, 1 page.
J. A. McAteer et al., "Shock Wave Injury to the Kidney in SWL: Review and Perspective", AIP Publishing, Conference Proceedings, 2007, vol. 900, pp. 287-301, 2007, 16 pages.
N. Bhojani and J. E. Lingeman, "Shockwave Lithotripsy—New Concepts and Optimizing Treatment Parameters", Urol. Clin. North Am., 2013, vol. 40, Issue 1, pp. 59-66, 8 pages.
N. R. Owen et al., "The use of resonant scattering to identify stone fracture in shock wave lithotripsy", J. Acoust. Soc. Am., 2007, vol. 121, Issue 1, pp. EL41-EL47, 8 pages.
F. Fernandez et al, "Treatment time reduction using tandem shockwaves for lithotripsy: An in vivo study," J. Endourol. 2009, vol. 23, Issue 8, pp. 1247-1253, 8 pages.
D. L. Sokolov et al., "Use of a dual-pulse lithotripter to generate a localized and intensified cavitation field," J. Acoust. Soc. Am., 2001, vol. 110, Issue 3, pp. 1685-1695, 12 pages.

* cited by examiner

DIBUJOS

SYSTEM FOR THE CONTROLLED FRAGMENTATION OF SOLIDS BY MEANS OF VORTEX SOUND BEAMS

CROSS-REFERENCE TO RELATED APPLICATIONS AND PRIORITY

This patent application claims priority from PCT Application No. PCT/ES2021/070524 filed Jul. 15, 2021, which claims priority from Spanish Patent Application No. P202030757 filed Jul. 20, 2020. Each of these patent applications are herein incorporated by reference in their entirety.

FIELD OF THE INVENTION

The present invention relates to technologies for the interaction of ultrasonic acoustic beams with biological tissues and matter. More specifically, the invention relates to an acoustic vortex beam system for the fragmentation of hardened masses or calculi, in a minimally invasive manner. In said system, the vortex beams can be modulated in intensity, phase, repetition rate, topological charge, etc., according to the size, location, and composition of the mass to be destroyed, as well as the energy that said beam transfers to the mass.

BACKGROUND OF THE INVENTION

Until the early 1980s, most renal calculi were treated with open surgery. Advances in minimally invasive ureterorenoscopy (URS) and percutaneous nephrostolithotomy (or nephrolithotomy) (PCNL) techniques, together with the advent of non-invasive extracorporeal shockwave lithotripsy (ESWL) systems, have led to the abandonment of open surgical treatments to remove renal calculi and/or gallstones, as reported for example in N. Bhojani and J. E. Lingeman, "*Shockwave Lithotripsy—New Concepts and Optimizing Treatment Parameters*", Urol. Clin. North Am., vol. 40, no. 1, p. 59-66, 2013.

The first ESWL treatment was performed in 1980 in Germany, using a Dornier "Human Model 1" (HM1) lithotripter (see C. Chaussy et al., "*Extracorporeally Induced Destruction of Kidney Stones by Shock Waves*", Lancet, vol. 316, no. 8207, p. 1265-1268, 1980). The clinical use of the ESWL lithotripsy technique has rapidly become widespread for the fragmentation of kidney stones due to its effectiveness and reduced side effects.

In contrast to URS and PCNL, the aim of ESWL treatments is calculus fragmentation, not calculus extraction. This is achieved by subjecting the calculus to a series of high amplitude ultrasonic pulses. These pulses are mechanical waves that produce shear stresses within the calculi and high internal stresses. After being subjected to such mechanical stresses, the calculus fractures into smaller fragments that are naturally expelled by the organism itself (see J. J. Rassweiler et al., "*Shock Wave Technology and Application: An Update*"; Eur. Urol., vol. 59, no. 5, p. 784-796, 2011).

The acoustic energy of ESWL is concentrated in a relatively small area, which surrounds the focal point of the lithotripter and is the location of the kidney calculus of interest. The focal zone can be small or large, and the amount of energy or the maximum pressure applied to same can be manipulated. Typical focusing values for modern lithotripters are pressures of between 50 and 150 MPa, delivered to a focal zone of between 3 and 6 mm, as mentioned in C. Chaussy et al. referred to above. However, a high focusing does not ensure the effectiveness of the treatment. More focused lithotripters tend to have fewer shock waves that actually impact the calculus, leaving a remnant of shock wave energy that is deposited directly into the renal tissue (see R. O. Cleveland et al., "*Effect of Stone Motion on in Vitro Comminution Efficiency of Storz Modulith SLX*", J. Endourol., vol. 18, no. 7, p. 629-633, 2004). Since the calculus will be more likely to remain within the focal zone during treatment if the zone is larger, there are devices that work with lower pressures and larger focal regions, e.g. 20 MPa over a 20 mm focus. Wide focal zone lithotripters produce smaller renal lesions and are therefore more advantageous, as reported in the literature references (see A. P. Evan et al., "*Independent assessment of a widefocus, low-pressure electromagnetic lithotripter: absence of renal bioeffects in the pig*", BJU Int, vol. 101, no. 3, p. 382-388, 2008; J. A. McAteer et al., "*Independent Evaluation of the Lithogold LG-380 Lithotripter: In Vitro Acoustic Characteristics and Assessment of Renal Injury in the Pig Model*", J. Urol., vol. 181, no. 4, p. 665-666, 2009). In addition, it has been shown that the shear waves required to cause large internal stresses increase when the focal width is larger than the calculus diameter (see R. O. Cleveland and O. A. Sapozhnikov, "*Modeling elastic wave propagation in kidney stones with application to shock wave lithotripsy*", J. Acoust. Soc. Am., vol. 118, no. 4, p. 2667-2676, 2005).

Currently, all lithotripters require four common elements: a mechanism for generating high-intensity ultrasonic waves, a mechanism for focusing said waves, a coupling means between the generation system and the patient's body, and a system for locating the calculi for treatment planning and monitoring.

There are three main types of technologies for generating ultrasonic waves: electrohydraulic, piezoelectric and electromagnetic systems.

First, electrohydraulic generation systems produce shock waves by means of an electric arc located over a first focus, $F_1$, of an ellipsoidal reflector. The device is positioned so that the calculus is located over the second geometric focus of the ellipsoidal reflector, commonly referred to as $F_2$. Thus, the shock wavefront propagates from the first focus, going through a water bath which in turn serves as an acoustic coupling with the patient's body, to the second geometric focus of the ellipsoidal reflector, where the calculus is located.

Secondly, piezoelectric systems are based on the vibration of piezoelectric materials subjected to an electric field, commonly generated by a short high-voltage pulse between two electrodes. The expansion and compression of the piezoelectric actuators produces an ultrasonic wave that propagates to a focal point of the system, where the calculi are located. When piezoelectric systems are made up of many elements, they constitute phased arrays (also known as arrangements), which allow electronic focusing by means of the time lag of the electric pulses, allowing the focal point to be dynamically positioned, as disclosed in the previously referenced J. J. Rassweiler et al. paper and in T. G. Leighton and R. O. Cleveland, "*Lithotripsy*", Proc. Inst. Mech. Eng. Part H J. Eng. Med., vol. 224, no. 2, p. 317-342, 2010.

Finally, electromagnetic lithotripters use an electrodynamic transducer consisting of a coil placed against a thin metal membrane in contact with water. A high-voltage pulse is discharged across a capacitor to generate a current pulsed by the coil. The subsequent current pulse through the coil induces a repulsive force on the metal membrane, which violently compresses the water generating an ultrasonic pulse. This process is described in detail in several prior art references, as for example in J. J. Rassweiler et al. cited above or in W. Folberth et al., "*Pressure distribution and energy flow in the focal region of two different electromagnetic shock wave sources*"; *J. Stone Dis.*, vol. 4, no. 1, p. 1-7, 1992. Pulse focusing is achieved by using an acoustic lens or a parabolic reflector (see the T. G. Leighton and R. O. Cleveland papers previously referred to).

One of the mechanisms of stones breakage is the activation of cavitation bubbles which are produced around the stone. There are lithotripters that seek to optimize this phenomenon, for example, by using simultaneous shock waves or shock waves in rapid succession, to generate the collapse of the bubbles against the stone. One strategy to achieve this is to generate, by means of a second piezoelectric head, a second shock wave confocal to the first one, which significantly improves the fragmentation of the stone, which is well known through references X. Xi and P. Zhong, "*Improvement of stone fragmentation during shock-wave lithotripsy using a combined EH/PEAA shock-wave generator-in vitro experiments,*" *Ultrasound Med. Biol.* vol. 26, no. 3, p. 457-467, 2000 and A. Z. Weizer et al., "*New Concepts in Shock Wave Lithotripsy,*" *Urol. Clin. North Am.* vol. 34, no. 3, p. 375-382, 2007 Another strategy is to add an extra electrical excitation system to the lithotripter to produce two consecutive pulses, as disclosed in F. Fernandez et al, "*Treatment time reduction using tandem shockwaves for lithotripsy: An in vivo study,*" *J. Endourol.* vol. 23, no. 8, p. 1247-1253, 2009. Finally, dual-head lithotripters can deliver shockwaves at the same point to optimize fragmentation, as carried out in D. L. Sokolov et al., "*Use of a dual-pulse lithotripter to generate a localized and intensified cavitation field,*" *J. Acoust. Soc. Am.*, vol. 110, no. 3, p. 1685-1695, 2001 and in D. L. Sokolov et al., "*Dual-pulse lithotripter accelerates stone fragmentation and reduces cell lysis in vitro,*" *Ultrasound Med. Biol.* vol. 29, no. 7, p. 1045-1052, 2003.

Two methods of coupling between the ultrasound generating system and the patient's body are commonly used. The first method, called water bath lithotripter, partially immerses the patient's body in water to ensure proper transmission of the shock waves into the tissues. The second method, called dry head lithotripter, consists of covering the emitting system with a water balloon and coupling it by means of an elastic membrane in contact with the patient's skin (see the T. G. Leighton and R. O. Cleveland papers cited above). In this last technique it is critical to ensure a correct impedance coupling between the membrane and the skin using coupling gel. It is necessary to avoid the occurrence of bubbles in the gel, which drastically diminish the effectiveness of ESWL, as demonstrated by Y. A. Pishchalnikov et al, "*Air Pockets Trapped During Routine Coupling in Dry Head Lithotripsy Can Significantly Decrease the Delivery of Shock Wave Energy,*" *J. Urol.* vol. 176, no. 6, p. 2706-2710, 2006.

It is known that the use of different sequences during the generation of ultrasonic beams, as power ramps with a short pause, improve ESWL calculus fragmentation results, in addition to reducing renal tissue injury. The use of slow repetition rates of around 60 waves per minute results in optimal fragmentation with minimal complications.

Imaging techniques such as X-ray or fluoroscopy are generally used to identify and locate the calculus. This also allows the focal point of the system to be aligned on the solid to be fragmented (e.g. a kidney calculus) before starting ESWL treatment. However, a major drawback is the movement of the calculus relative to the focal point of the lithotripter during treatment. This is mainly due to the patient's respiratory movement. If no measures are taken, this results in 50% or more of the delivered shock waves not reaching the calculus and striking the renal tissue, overheating it and even damaging it. To avoid this, dynamic tracking and focusing systems have been developed using ultrasound imaging and piezoelectric lithotripters that continuously locate the calculus and synchronise the shock wave triggering (see C. Bohris et al., "*Hit/miss monitoring of ESWL by spectral Doppler ultrasound*"; *Ultrasound Med. Biol.*, vol. 29, no. 5, p. 705-712, 2003) or optical lithotripters.

Recently, acoustic systems for monitoring stone fragmentation have been proposed. Using a broadband receiver, acoustic signals are acquired from the reverberation and resonance of stones under the action of ultrasound. Various parameters, such as the frequency of the acquired signals, correlate with the size of the fragment (see N. R. Owen et al., "*The use of resonant scattering to identify stone fracture in shock wave lithotripsy*"; *J. Acoust. Soc. Am.*, vol. 121, no. 1, p. EL41-EL47, 2007). This allows treatment monitoring, as well as knowing when treatment needs to be stopped and reducing unnecessary acoustic energy on healthy renal tissue.

However, although ESWL is widely accepted and widely used, this procedure has some important limitations. First, certain renal calculi are very resistant, such as calculi made up of brushite, and their fragmentation by ESWL is limited. This drawback is extremely important because patients with such stones will be subjected to ESWL and thus exposed to its (minor and major) complications without the achievable benefit of fragmentation (see S. C. Kim et al., "*Cystine calculi: Correlation of CT-visible structure, CT number, and stone morphology with fragmentation by shock wave lithotripsy*"; *Urol. Res.*, vol. 35, no. 6, p. 319-324, 2007).

The location, size, and composition of the calculi are the most important predictors of the success of ESWL treatment. The different types of calculi, in decreasing order of hardness and therefore difficulty of fragmentation, consist of brushite (calcium hydrogen phosphate), cystine, calcium oxalate monohydrate, struvite, calcium oxalate dihydrate, or uric acid. The type of calculus can be identified by measuring the radiodensity by X-ray computed tomography. Calculi with densities above 900 Hounsfield units (HU) anticipate a possible failure of ESWL treatment (see L. J. Wang et al., "*Predictions of outcomes of renal stones after extracorporeal shock wave lithotripsy from stone characteristics determined by unenhanced helical computed tomography: A multivariate analysis*"; *Eur. Radiol*, vol. 15, no. 11, p. 2238-2243, 2005). X-ray based techniques are used as predictors of calculus fragmentation by ESWL. Other calculi do not fragment completely and complementary treatments are needed, as is often the case with calculi made up of calcium oxalate monohydrate or cystine. Finally, mainly due to the action of shock waves on healthy tissues, minor complications are very frequent, in addition to major complications in some cases (see J. A. McAteer et al., "*Shock Wave Injury to the Kidney in SWL: Review and Perspective*" p. 287-301, 2007).

Current advances in optimizing ESWL results focus on the optimization of treatment parameters, such as the initial characterization of the type, location, and size of the stones (or calculi), optimizing the acoustic coupling and the repetition rate of the waves, as well as the sequence of the shock waves.

However, since the tissues surrounding the calculus to be fragmented are always subjected to high-intensity ultrasound pulses, these tissues are exposed to minor or major complications. These complications include hemorrhages, thrombi, arrhythmias, vasoconstriction, hypertension, reduced renal functionality, infections, alterations of the autonomic neural system, and the release of cellular mediators and hormones. The production of tissue damage has been identified with two consecutive stages. The first stage consists of initial tissue rupture due to mechanical effects of shock waves. This results in an accumulation of blood. In a second stage, such accumulation facilitates the occurrence of inertial cavitation in the focal zone, producing the most detrimental effects on the tissues (see the T. G. Leighton and R. O. Cleveland papers previously referred to). The occurrence of inertial cavitation is intimately linked to the amplitude of shock wave rarefaction, i.e., the minimum pulse pressure. Finally, an excess of cavitation generates gas bubbles that act as a barrier to shock waves (see K. Maeda et al., "*Energy shielding by cavitation bubble clouds in burst wave lithotripsy,*" *J. Acoust. Soc. Am.* vol. 144, no. 5, pp. 2952-2961, 2018). For all these reasons, it is necessary to quantify the cavitation that occurs, with different cavitation indices being disclosed in the field of fluid mechanics.

Furthermore, although patients previously experience significant pain from renal calculi, ESWL techniques also induce so much pain that in some cases treatment has to be aborted mid-procedure (see the T. G. Leighton and R. O. Cleveland papers cited above). Although lower focused sources (and thus lower amplitudes of acoustic waves) are now used to reduce pain, this remains a major limitation of the state of the art.

On the other hand, acoustic beam focusing technologies are known, as disclosed, for example, in U.S. Pat. No. 4,865,042 (Unemura et al.), "Ultrasonic irradiation system", which proposes a system of multiple ring acoustic transducers, whose excitation signals have been suitably phased lag to achieve focusing in a two-dimensional (2D) planar focal zone (annular or elliptical in shape), avoiding unwanted secondary focusing along the direction of propagation. A more recent example, concerning three-dimensional (3D) helical vortex beams, is disclosed for example in N. Jimenez et al., "*Sharp acoustic vortex focusing by Fresnel-spiral zone plates,*" *Applied Physics Letters,* 2018, vol. 112, no 20, p. 204101. The vortex beam is a longitudinal mechanical wave, having a frequency typically in the ultrasound range, wherein the corresponding acoustic field presents a phase singularity along one axis. In particular, in cylindrical coordinates $r=r(\theta,r,z)$ such a beam can be expressed as:

$$P(\theta,r,z)=P_0 G_r(r)G_z(z)\exp(iM\theta), \qquad (1)$$

wherein $P_0$ is an arbitrary value of pressure, while $G_r(r)$ and $G_z(z)$ describe the beam shape along the radial (r) and axial (z) coordinates, respectively, M is the topological beam charge (related to momentum transfer efficiency) and a is the azimuthal coordinate. Phase dislocation (typically, screw-like) produces a null field on the axis of the acoustic beam due to destructive wave interference at that point, as illustrated in FIG. 1. The maximum of the field has an annular or toroidal shaped distribution around the focus. However, the phase of the field ($\phi$) varies linearly along the azimuthal coordinate, so the pressure maximum rotates as a function of time. This causes the vortex beams to transfer linear and angular momentum to the interacting matter very efficiently. In addition, they allow the energy transferred to said matter to be dosed, since they can be designed to be focused on a specific region and with certain physical parameters (intensity, frequency, wave repetition rate, etc.). In this case, these vortex beams make it possible to reach a volumetric 3D focal zone, so that simultaneously and without the need to readjust the focus (electronically or mechanically) a 3D focal zone can be reached, in an intentional and controlled manner, which is not limited to a 2D plane.

In summary, it is necessary to develop new techniques that allow the efficient fragmentation of stones using mechanical waves with reduced amplitudes to minimize the pain suffered by the patient, as well as the adverse effects and complications of the usual extracorporeal shock wave lithotripsy procedures.

BRIEF DESCRIPTION OF THE INVENTION

The present invention discloses a system for the non-invasive fragmentation of solids, using acoustic vortexes. It should be noted that one of its most important applications is its use in lithotripsy.

In a particular application, the object of the invention provides a solution to the problem of the poor efficiency of ESWL techniques in terms of the amount of energy that does not end up being applied to the solids to be fragmented (e.g., gallstones or renal calculi), but to the surrounding soft tissue. In this sense, the invention surpasses the current state of the art and provides the methods and system necessary to fragment calculi inside tissues, in a non-invasive manner and using finite amplitude focused ultrasonic vortex beams, also commonly known as high-intensity ultrasonic beams. However, this application is not limiting and can be adapted for other applications requiring the controlled destruction of solids in a non-invasive manner.

In a first inventive aspect, the invention relates to a system for the controlled fragmentation of solids by means of acoustic shock waves, comprising at least:
   a) one acoustic beam generation unit which, in turn, comprises:
      an electric pulse generation subsystem, said pulses being characterized by a voltage and/or current suitable for producing the fragmentation of solids.
      a first transduction subsystem, adapted for converting electric pulses into high-intensity acoustic waves or pressure; where said transduction may be electrohydraulic, electromagnetic, piezoelectric, or of any kind.
      an acoustic beam generation subsystem for generating acoustic beams from the acoustic waves produced by the transduction subsystem and for focusing said beams in a focal volume in which the solid or solids to be fragmented are located.
      an acoustic coupling subsystem, adapted for coupling the acoustic beams to the solid or solids to be fragmented and thus minimize the attenuation produced during the propagation of the acoustic waves to the focus of the system.
      a positioning subsystem, adapted for adjusting the position of the focal point. Said positioning subsystem can be electromechanical and allows the position of the focus to be adjusted automatically or manually, as required by the system operator or user.
   b) one feedback and control unit, which allows to modify the orientation and intensity of the acoustic waves striking the solid or solids to be fragmented, and comprising:
      a control subsystem, which controls the acoustic beam generation unit.
      a second transduction subsystem, adapted for the acquisition of information relating to the acoustic beams before and after interacting with the solid or solids.
      a processing subsystem for processing the information acquired by the second transduction subsystem.

Advantageously, in said system, the acoustic beams are acoustic vortex beams, and the feedback and control unit further comprises a feedback subsystem, configured to receive the information processed by the processing subsystem and send it to the control subsystem.

In preferred embodiments of the invention, the acoustic vortex beams are high-intensity ultrasonic acoustic vortex beams. Said vortex beams are focused on the calculi, producing torques, shearing stresses, and high internal stresses that efficiently fragment said calculi. As a result of the acoustic vortexes, the ultrasonic excitation energy (in the form of longitudinal waves) is very efficiently converted into mechanical energy (as transverse waves). Since the generation of shearing stresses is more efficient using this type of beam, the ultrasonic field amplitude needed to fragment the calculi are much lower than in current extracorporeal shock wave lithotripsy techniques, thereby reducing unwanted effects on soft tissues such as hemorrhages in surrounding tissues or damage due to cavitation. Acoustic vortex generation technology is known and is not an intrinsic part of the object of the patent. In fact, multiple vortex beam configurations can serve this purpose provided that they allow the phase dislocation to be adjusted along an axis.

In other embodiments of the invention, the feedback and control unit further comprises an imaging subsystem; and it also comprises a monitoring subsystem for monitoring the solid or solids, including means for the graphical representation to offer information about the fragmentation method to a user of the system. The imaging system allows monitoring of the solid (location, tracking, and measurement of the position thereof and its surroundings). In other preferred embodiments of the invention, to control the dosing of energy applied to the solid, sensors can be included to measure the temperature around the focus. In an advantageous embodiment of the invention, the monitoring subsystem comprises methods of pulse echo ultrasonic imaging. In other embodiments of the invention, it is additionally possible to use other imaging methods (fluoroscopy, X-rays, etc.), which may in turn require other transduction mechanisms. As a result of the monitoring subsystem, the user of the system can monitor treatment and decide to interrupt same if needed (for example, if the patient reports pain or if the acoustic waves have an excessive amplitude).

In some preferred embodiments of the invention, the information processing subsystem comprises real-time measurements of the cavitation produced around the focal point, and wherein the feedback subsystem further takes into account at least the evolution or the state of said cavitation for readjusting the physical parameters describing the acoustic beams striking the focus. For example, if there is excessive cavitation, then the amplitude or the repetition rate of the acoustic beams can be reduced.

In some particular embodiments of the invention, the first electromechanical transduction subsystem is of the electrohydraulic type, and the acoustic beam generation subsystem comprises a reflector with a helical-ellipsoidal surface for generating the vortex in reflection. In this case, the positioning subsystem is of the mechanical type and is in charge of aligning the focus of the system with the solid to be fragmented.

In other preferred embodiments of the invention, the first transduction subsystem is of the electromagnetic type, and the acoustic beam generation subsystem comprises a helical-paraboloidal reflector. Additionally, in said embodiments, the positioning subsystem is preferably of the mechanical type and serves for aligning the focus of the system with the solid to be fragmented.

In other advantageous embodiments of the invention, the first transduction subsystem is of the electromagnetic type, while the acoustic beam generation subsystem comprises an acoustic lens. Said lens requires a mechanical positioning subsystem for adjusting the focus. In other even more advantageous embodiments, the acoustic lens has a helical or helical-ellipsoidal phase profile.

In another particular implementation of the invention, the first transduction subsystem for generating the beams is of the piezoelectric type. In this case, the acoustic beam generation subsystem comprises a multiple element phased array immersed in a fluid. Unlike the particular embodiments above, the positioning system is preferably of the electronic type and allows the delays applied to the excitation signal of each of the channels of the phased array to be configured to readjust the position of the focus of the system without the need for mechanical alignment.

In a further embodiment of the invention, the first transduction subsystem comprises a single piezoelectric transducer immersed in a fluid, with the arrangement of said transducer on a helical-spheroidal surface being what provides the acoustic beam generation subsystem; said system further comprising a positioning subsystem of the mechanical type for adjusting the focal point of the system.

Another additional embodiment of the invention consists of replacing, in the previous embodiment, the single transducer with a multiple element piezoelectric transducer, wherein each element is arranged on the helical-spheroidal surface. In this sense, in this embodiment the first transduction subsystem comprises a multiple element piezoelectric transducer immersed in a fluid, with the arrangement of each of the channels thereof on a helical-spheroidal surface being what provides the acoustic beam generation and focusing subsystem; said system further comprising a positioning subsystem of the mechanical type for adjusting the focal point of the system.

Another preferred embodiment of the invention includes a first transduction subsystem of the piezoelectric type for generating acoustic waves, wherein the acoustic beam generation (and focusing) subsystem further comprises an acoustic lens. In some even more advantageous embodiments, said acoustic lens can have a helical or helical-ellipsoidal phase profile.

A preferred use of the system for the fragmentation of solids consists of its application in the field of lithotripsy.

In a further preferred embodiment of the invention, the feedback and control unit comprises a plurality of actuators for readjusting the focus of the system according to the patient's movement, for example, for offsetting the misalignment of the focus introduced by the patient's breathing. In such a case, the actuators can be pressure pads, abdominal pneumatic sensors, tracheal breath sound monitors or analogous sensors for detecting breathing. This realignment of the focus is preferably carried out in real time.

In the scope of the invention, arrays or phased arrays or arrangements are preferably understood to be a matrix of acoustic transducers wherein each element can be adjusted to emit a beam with certain physical characteristics (amplitude, frequency, phase, etc.). The transducers, in turn, can be of a single element (a single transducer) or divided into multiple elements (also known as sectors or channels), each of which acts as an independent transducer. In turn, an acoustic lens is understood to be a device capable of focusing sound similarly to how an optical lens focuses light.

In the context of the invention, once the acoustic waves are formed and oriented towards the position where they are to act, they are referred to as acoustic beams. An acoustic beam refers to the already formed acoustic wave.

Furthermore, vortex beam shall be understood as an acoustic beam, whether two-dimensional or three-dimensional, whose acoustic field has a phase dislocation along an axis (referred to as 'axis of propagation'). Thus, A 2D vortex beam could be annular or ellipsoidal in shape, while a 3D beam could be helical in shape. The zone on which said beam is focused is a focal volume, in 3D, extending along the direction of propagation of the beam. The focus of the system shall preferably be understood to be a region corresponding substantially with the centroid of said focal volume. In the scope of the invention, the expression "substantially" shall likewise be understood to be identical or comprised within a margin of variation of ±15%.

DESCRIPTION OF THE DRAWINGS

To complement the description of the invention, a set of figures is attached, forming an integral part of the description and illustrating several preferred implementations of the invention. However, such implements should not be understood to be restrictive of the scope of the invention, but rather simply different examples of how the invention can be carried out.

REFERENCE NUMBERS USED IN THE DRAWINGS

| | |
|---|---|
| (1) | Electric pulse generation subsystem |
| (2) | First transduction subsystem |
| (3) | Acoustic beam generation subsystem |
| (4) | Acoustic coupling subsystem |
| (5) | Positioning subsystem |
| (6) | Treatment (application of the acoustic beams to the solid to be fragmented) |
| (7) | Control subsystem (of the acoustic beam generation subsystem) |
| (8) | Second transduction subsystem |
| (9) | Imaging subsystem |
| (10) | Monitoring subsystem |
| (11) | Information processing subsystem |
| (12) | Feedback subsystem |
| (13) | Vortex beam |
| (14) | Focal point of the system (preferably coincides substantially with the position of the calculus or mass to be fragmented) |
| (15) | Helical-spheroidal surface |
| (100) | Acoustic beam generation unit |
| (200) | Feedback and control unit |

DETAILED DESCRIPTION OF THE INVENTION

Figure 1:
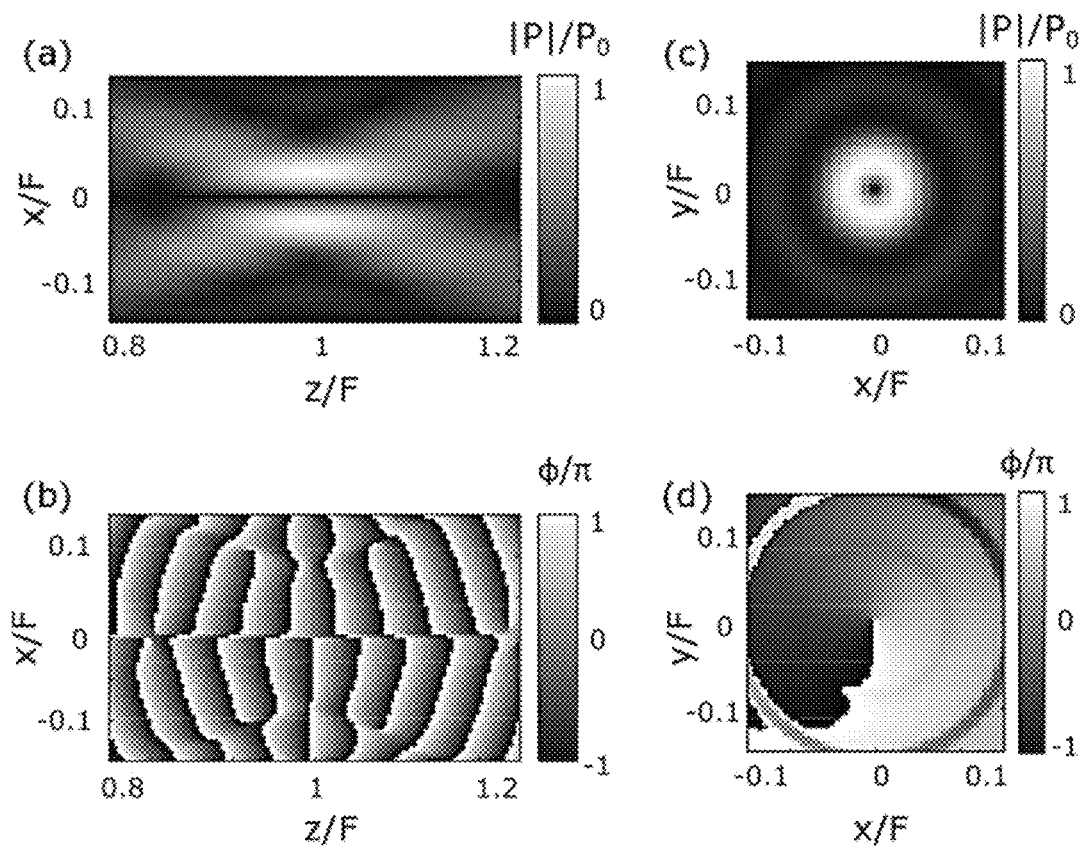
FIG. 1 shows the acoustic field of a focused vortex beam: (a) absolute value of the normalized acoustic field, denoted as $|P|/P_0$, in a sagittal section $P(x,y=0,z)$. (b) phase $\phi$ of the acoustic field in a sagittal section. (c) absolute value of the normalized acoustic field in a transverse section over the focal zone, $P(x,y,z=F)$. (d) phase of the acoustic field in a transverse section with respect to the focal zone.
Figure 2:
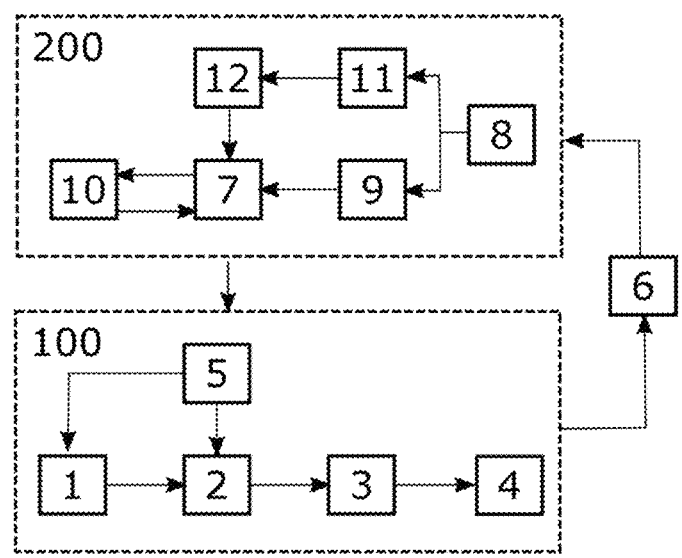
FIG. 2 shows a diagram of the system for the fragmentation of solids by means of (ultrasonic) acoustic vortexes which is an object of the invention, for its application in lithotripsy.

FIG. 2 shows a preferred embodiment of the system for the fragmentation of solids of the invention. Said system preferably comprises at least two units: an acoustic beam generation unit (100), which is preferably ultrasonic and high-intensity, and a feedback and control unit (200).

First, the acoustic beam generation unit (100) is in charge of the production of acoustic beams, which are preferably ultrasonic, and suitably orienting them in the zone where the calculus is located, for the purpose of causing their fragmentation. This unit (100) is formed by at least the following subsystems:

- a electronic power generation subsystem (1), adapted for generating high-voltage and/or high-current electric pulses.
- a first transduction subsystem (2) (preferably electromechanical) for converting electric pulses provided by the generation subsystem (1) into high-intensity ultrasonic waves.
- an acoustic beam generation subsystem (3), in charge of generating and orienting one or more vortex beams from the ultrasonic waves obtained in the first transduction subsystem (2).
- an acoustic coupling subsystem (4) between the acoustic beam generation unit (100) and the object to be fragmented (for example, a calculus inside the patient's body), to minimize attenuation of the ultrasonic waves constituting the vortexes during propagation, which has a very negative impact on the efficiency of the treatment (6).
- a positioning subsystem (5), which can be electronic or mechanical, which allows the focus of the beams formed and focused by the acoustic beam generation subsystem (3) to be aligned and thus strike the location where the calculus to be fragmented is located.

Once the acoustic beam generation unit (100) is configured, it then applies the treatment (6), which consists of directing the acoustic waves towards the solid to be fragmented.

In reference to the feedback and control unit (200) for the treatment, said unit is in charge of acquiring information about the position, characteristics and state of the calculus before, during, and/or after treatment (6). Based on the estimation of the position and size of the calculus, the unit (200) provides control signals which allow adjusting the position of the focal position (14) of the system and, where appropriate, other parameters of the vortex (topological charge, etc.). In general, the unit (200) consists of at least the following elements:

- a control subsystem (7) of the ultrasonic vortex beam generation subsystem (3), configured to modify the physical parameters of the beams (amplitude, intensity, frequency, etc.) by manipulating one or more of the subsystems (1, 2, 3, 4, 5) of the acoustic beam generation unit (100). Said subsystem (7) must allow the voluntary interruption of treatment by the system operator (for example, if the patient were to report excessive pain), or else the automatic stoppage of the electric pulse generation subsystem (1) should any critical threshold be exceeded (whether it is an excess temperature in the areas surrounding the treated zone or a too high cavitation index).
- a second transduction subsystem (8), which is electromechanical, configured to acquire signals of the acoustic beams before, during, and/or after treatment.
- a imaging subsystem (9) for imaging the solid to be fragmented and/or its surrounding areas. Preferably, the images are ultrasonic.
- a monitoring subsystem (10) for monitoring treatment, preferably in real time, comprising a monitor or any means for the graphical representation to offer information about the treatment to operator who is manipulating the system and, in particular, to show the images of the solid and other parameters of interest derived from same. The tracking information for the solid (calculus) provided by the monitoring subsystem (10) is used to adjust the focus of the high-intensity acoustic beam generation unit (100).
- a processing subsystem (11) for processing the acquired information, including means for analyzing its energy in different frequency bands of interest, for the purpose of evaluating the effectiveness of treatment (6) in real time (for example, by calculating various cavitation indices or other similar parameters which might be relevant in predicting risks of serious complications during treatment), such that this information also appears on the monitor or means for the graphical representation of the monitoring subsystem (10).
- a feedback subsystem (12) which, based on the tracking of the calculus performed by the monitoring subsystem (10), on the information extracted by the information processing subsystem (11) (ultrasonic signals, etc.), and/or on other measurements (for example, temperature increase in the vicinity of the zone where the beam is being focused), informs the control subsystem (7) of the need to adjust the beams (for example, through modifications of the amplitude, frequency, and repetition rate of the electric pulse generation subsystem (1), etc.).

The elements within each subsystem (1, 2, 3, 4, 5, 7, 8, 9, 10, 11, 12) are preferably interconnected as illustrated in FIG. 2.

It should be noted that the feedback and control unit (200) and, in particular, the acquired information processing subsystem (11), are in charge of the calculus of different acoustic indices that modulate the feedback subsystem (12), which, in turn, communicates to the control subsystem (7) the modifications that must be made in the pulse generation subsystem. Said indices modulate, preferably in real time, the intensity of the pulses and, accordingly, the amplitude of the ultrasonic waves and the repetition rate of the pulses. For this purpose, the system calculates the cavitation indices by integrating the energy of the acquired signals and filtering across different bandwidths. The parameters defined below are not exclusive and a person skilled in the art could define other similar parameters. In particular, these acoustic indices are obtained from the Fourier transform of the acoustic signal, denoted as $P(\omega)$.

First, the stable cavitation index is defined as $$I_{SC} = \frac{1}{N-1} \sum_{n=2}^{N} |P(n\omega_0)|^2,$$

wherein $\omega_0$ is the fundamental frequency of the ultrasonic emission (whether it is the fundamental frequency of a sinusoidal burst or the center frequency of pulses in the case of pulsed excitation) and $N=\omega_{max}/\omega_0$, where $\omega_{max}$ is the maximum frequency allowed by the bandwidth of the acquisition system.

The subharmonic cavitation index ($I_{SH}$) is calculated from the subharmonic component power spectrum, i.e., $$I_{SH} = \left|P\left(\frac{\omega_0}{2}\right)\right|^2.$$

The ultraharmonic cavitation index ($I_{UH}$) is calculated by integrating the power spectrum of all the fundamental frequency ultraharmonics, i.e., $$I_{UH} = \frac{1}{N-1}\sum_{n=2}^{N}\left|P\left(\frac{2n-1}{2}\omega_0\right)\right|^2.$$

The inertial cavitation index ($I_{IC}$) is calculated by integrating the entire spectrum of the acoustic signal and subtracting the power spectrum of the fundamental frequency harmonics, as follows:

$$I_{IC} = \frac{1}{\omega_{max} - 2\omega_0}\sum\nolimits_{2\omega_0}^{\omega_{max}}|P(\omega)|^2 d\omega - \frac{1}{N}\sum\nolimits_{n=1}^{N}|P(n\omega_0)|^2.$$

Lastly, the broadband cavitation index ($I_{BB}$) is calculated by integrating the spectrum of the acoustic signal and subtracting the power spectrum of the fundamental frequency harmonics and ultraharmoncis, $$I_{BB} = \frac{1}{\omega_{max} - 2\omega_0}\sum\nolimits_{2\omega_0}^{\omega_{max}}|P(\omega)|^2 d\omega - \frac{1}{N}\sum\nolimits_{n=1}^{N}|P(n\omega_0)|^2 - I_{SH} - I_{UH}.$$

In this way, the signals of the cavitation indices vary based on cavitation activity around the focal point (14), where the calculus to be fragmented is preferably located. These indices are used to modulate the control signals of the power generation system by means of the acoustic feedback system. The indices are furthermore shown by means of a graphic interface for monitoring the treatment (6) in real time and providing information relevant to the tracking and/or voluntary interruption of treatment (6).

A number of preferred implementations of the acoustic beam generation unit (100) are described below.

Figure 3:
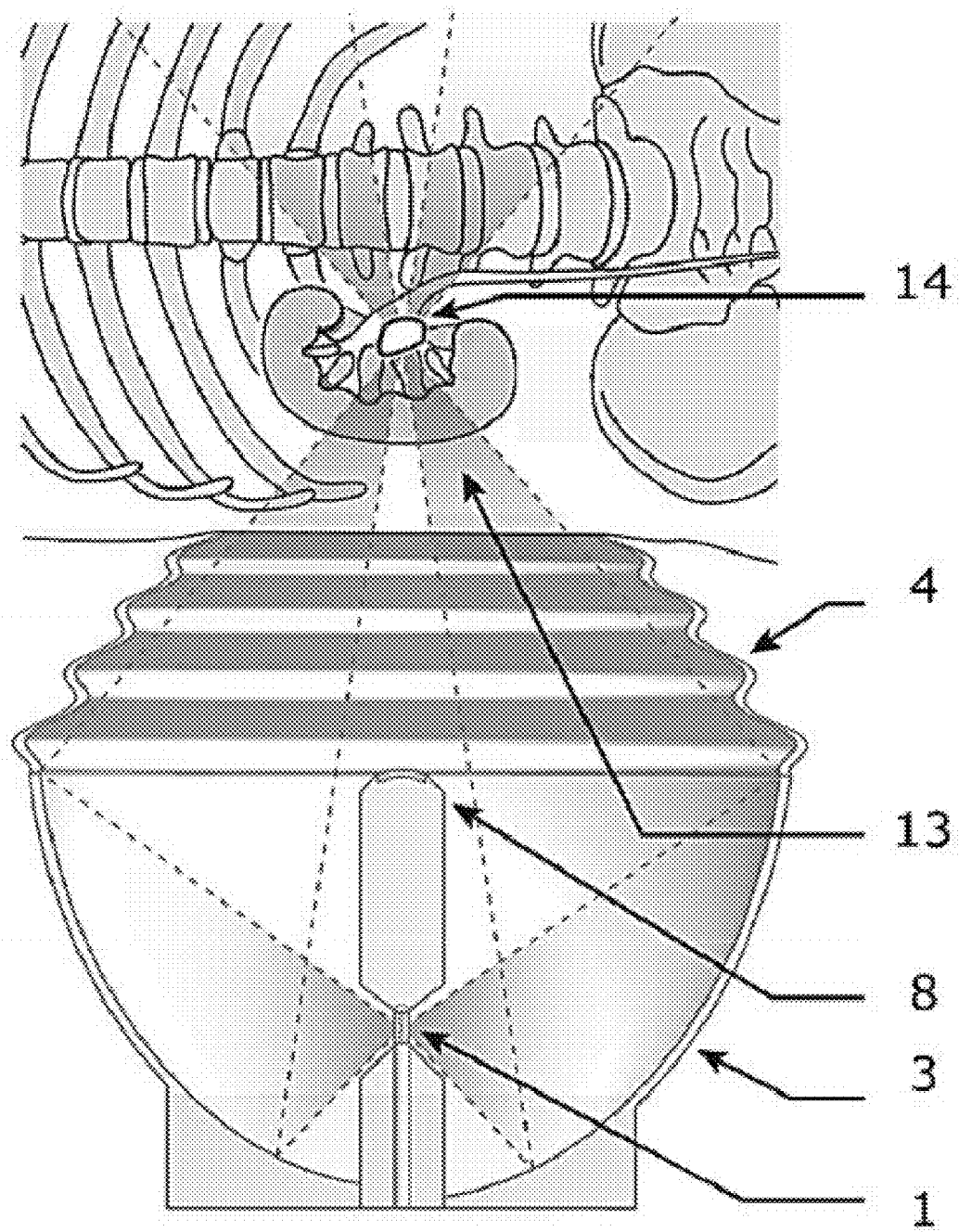
FIG. 3 depicts a scheme of a preferred implementation of the invention, wherein the acoustic beam generation subsystem (3) is of the electrohydraulic type and comprises a helical-ellipsoidal reflector. The vortex beams (13) are oriented towards the focal point (14) of the system, which coincides with the position of the solid (in this case, a kidney calculus) to be fragmented.

A preferred implementation of the invention is shown in FIG. 3, where the electric pulse generation subsystem (1) electrically excites a spark plug immersed in a fluid, which acts as a first electrohydraulic transduction subsystem (2). After subjecting the spark plug to a specific voltage, the dielectric is broken, generating an electric arc between its terminals. This induces a high current of electrons flowing between the two terminals, which results in a momentary increase in the temperature of the fluid. In turn, the temperature increase generates gas bubbles that expand violently and then compress under the hydrodynamic pressure of the rest of the fluid. This process produces a spherical, transient, high pressure amplitude acoustic wave that propagates throughout the fluid. The system comprises a reflector with a helical-ellipsoidal surface as the acoustic beam generation subsystem (3), in charge of reflecting the wavefront towards the position of the calculus to be fragmented.

Figure 4:
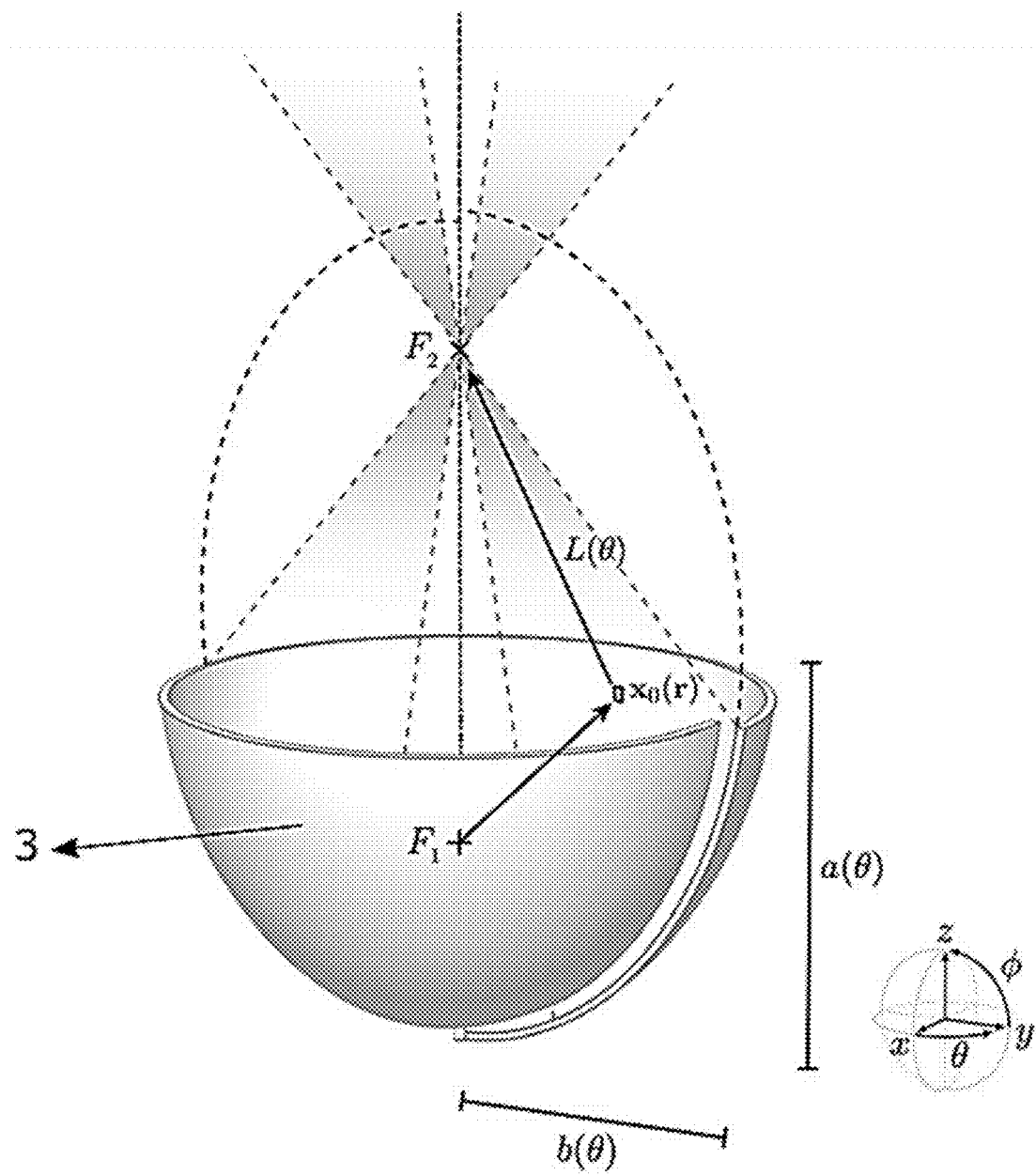
FIG. 4 illustrates in greater detail the helical-ellipsoidal reflector used for generating and focusing the vortex beams of FIG. 3.

Due to the particularities of the helical-ellipsoidal reflector, the vortex beam is generated in reflection and the wavefront is focused on the focal point $F_2$, according to the coordinate system shown in FIG. 4, where the fragmentation of the calculi will take place. To ensure optimal transmission of said wavefront, the system uses an acoustic coupling subsystem (4), which can be a water balloon coupled to the patient's skin by means of an elastic membrane, a layer of coupling gel, or a water bath. It should be noted that the helical-ellipsoidal reflector is arranged on a helical surface capable of providing an acoustic delay difference (at) as a function of the azimuthal coordinate (e) equal to:

$$\Delta t(\theta) = \frac{M\theta}{\omega_0}, \qquad (2)$$

where $\omega_0$ is the design angular frequency and M is the topological charge of the beam. Since the beam propagates in a fluid in which constant propagation speed can be assumed, such delays are generated when the acoustic path difference ($\Delta L$) is equal to:

$$\Delta L(\theta) = (M\lambda_0\theta)/2\pi, \qquad (3)$$

where $\lambda_0 = 2\pi c_0/\omega_0$ is the design wave length and $c_0$ is the speed of sound in the fluid. If an elliptical curve with foci $F_1$ and $F_2$ and an ellipsoid constant $a_p(\theta) = [2a - \Delta L(\theta)]/2$, where a is the largest of the minor semi-axes of the helical-ellipsoidal reflector, is defined, the semi-axes ($b_x$ and $b_y$) of the surface of the reflector can be defined based on the azimuthal coordinate, $b_x(\theta) = \sqrt{a_p(\theta)^2 - F_2^2}$ and $b_y(\theta) = \sqrt{a_p(\theta)^2 - F_2^2}$. Lastly, the surface of the helical-ellipsoidal reflector at a point r=r(x, and, z) is given by $F_2$:

$$x(\theta,\phi) = b_x(\theta)\cos(\theta)\sin(\phi), \qquad (4)$$

$$\text{and } (\theta,\phi) = b_y(\theta)\sin(\theta)\sin(\phi), \qquad (5)$$

$$z(\theta,\phi) = -F_2 - a_p(\theta)\cos(\phi), \qquad (6)$$

where in equations (4-6) the azimuthal angle $\theta$ is comprised between 0 and $2\pi$, and following convention, the angle of elevation $\phi$ is comprised between 0 and $\pi$. If it is further considered that the semi-axes of the reflector geometrically limit the aperture (A) thereof, A<2a, then the maximum elevation is given by $\phi_{max} = \tan^{-1}(A/2F_2)$ while the diameter of the central gap ($A_h$) between the electrohydraulic electric pulse generation subsystem (1) and the second transduction subsystem (8) used for monitoring treatment (6), determines that the minimum elevation is given by $\phi_{min} = \tan^{-1}(A_h/2F_2)$. At a very low frequency the reflector acts as an elliptical reflector since the phase difference is very low. Therefore, both at a low and at a high frequency, the helical-ellipsoidal reflector ensures that all the acoustic energy is focused on the focus $F_2$. Since the position of the focus cannot be electronically controlled and is set by the focus of the helical-ellipsoidal reflector, a mechanical movement system is needed to align the focal point (14), $F_2$, with the calculus. The main drawback of this implementation is its short service life due to the erosion of spark plugs because of use.

Figure 5:
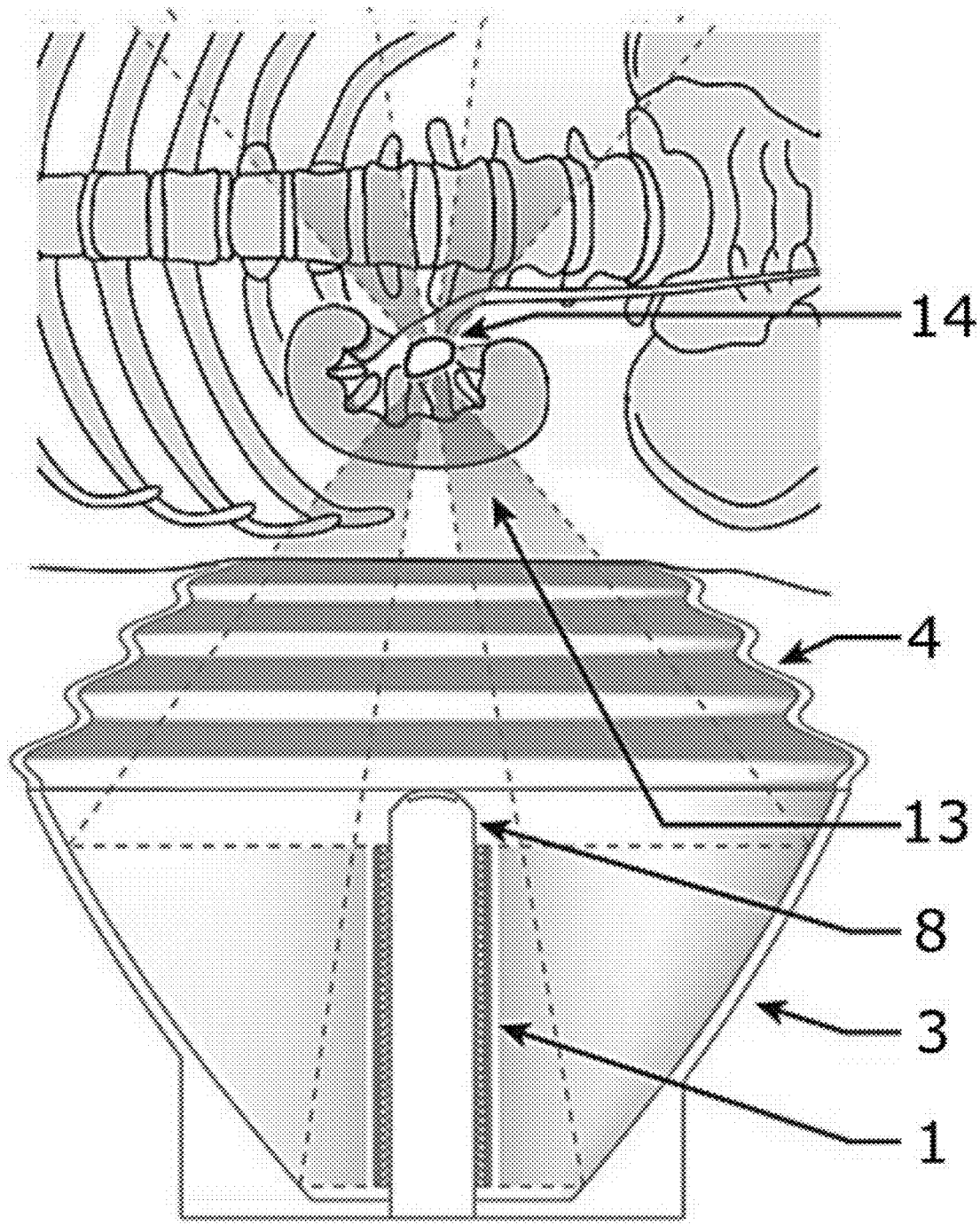
FIG. 5 depicts a scheme of a preferred implementation of the system of the invention, comprising an acoustic beam generation subsystem (3) of the electromagnetic type and including a helical-paraboloidal reflector. The vortex beams (13) are oriented towards the focal point (14) of the system, which coincides with the position of the solid to be fragmented.
Figure 6:
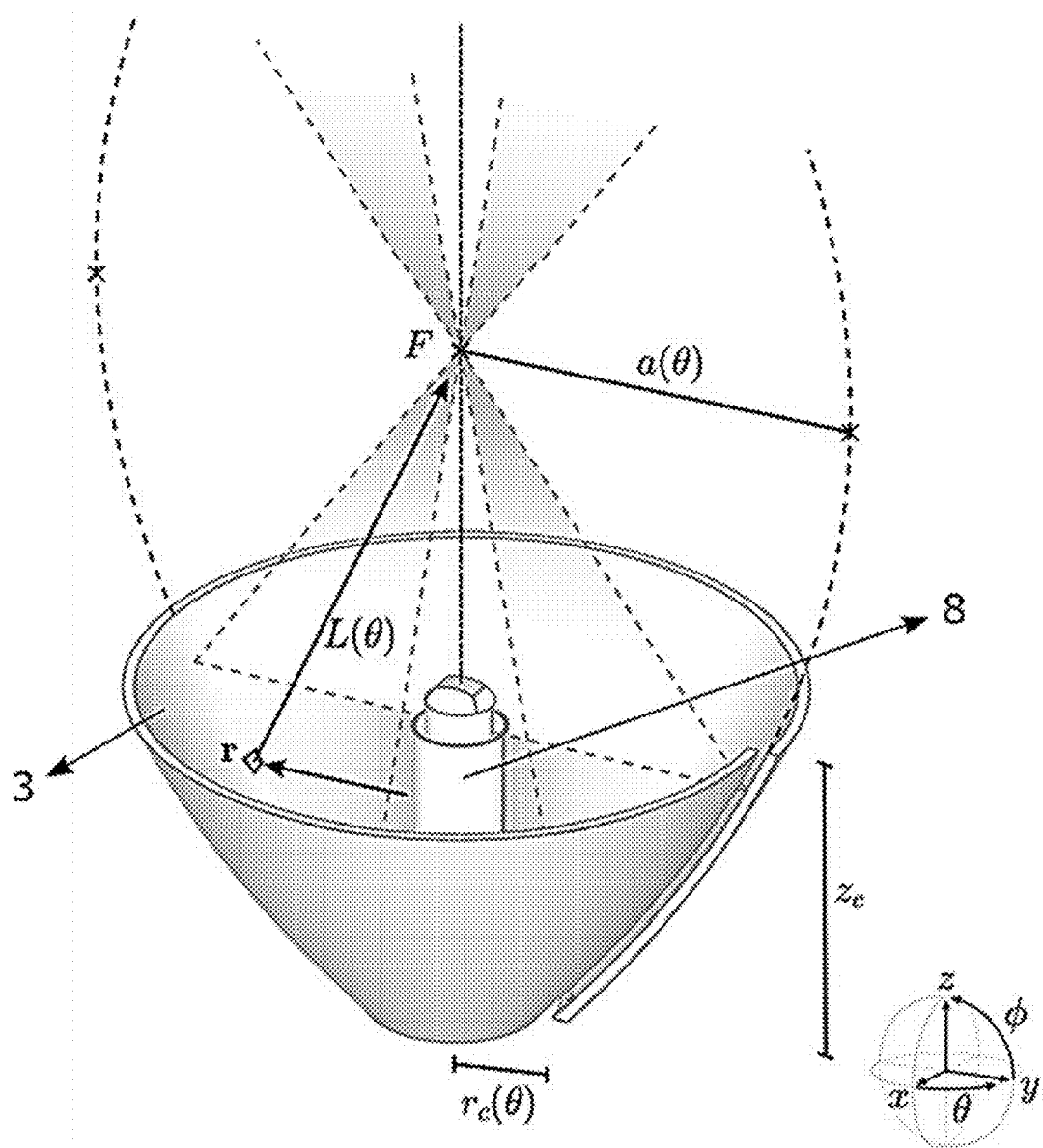
FIG. 6 includes a detailed diagram of the structure of the helical-paraboloidal reflector referred to in FIG. 5 and used for the acoustic beam generation subsystem (3), which is of the electromagnetic type.

In a preferred alternative implementation, the ultrasonic, high-amplitude acoustic (vortex) beam generation subsystem (3) requires the prior action of a first transduction subsystem (2) of the electromagnetic type and comprises a helical-paraboloidal reflector for generating and focusing the beam, as shown in FIG. 5. The system thereby uses a high-current electric pulse generation subsystem (1) for electrical excitation by means of a coil adhered to a movable elastic cylinder immersed in a fluid and located on the axial axis of the system. Similarly to electromechanical transducers existing in dynamic speakers, induction of the coil generates a force which first expands and then compresses the cylinder. Said electromagnetic transduction process produces high amplitude, transient, cylindrical pressure acoustic wavefront, which propagates along the fluid along the radial coordinate, perpendicular to the axial axis of the system. The reflector with a helical-paraboloidal surface is used to redirect said wavefront over the focal point (14), hereinafter referred to as F, where the fragmentation of the calculi will take place. The acoustic coupling subsystem (4) can be, among others, a water balloon coupled to the patient's skin by means of an elastic membrane, a layer of coupling gel, or a water bath. It should be noted that the design of the reflector (depicted in FIG. 6) simultaneously assures the focusing of the wavefront over the focal point and that a phase dislocation takes place over that point. To that end, the acoustic path difference must meet the conditions of Equations (2-3). The design of the reflector is done considering a surface helical-parabolic, formed by a parabolic profile the focus of which is set on point r(θ,r,z)=(0, 0,F). The parabolic profiles cut the lower plane of the system located at z=0 at point r(θ,r,z)=(θ,r$_c$(θ),0), wherein the coordinate rc(θ)=R$_m$−(m'Mθλ$_0$/2π), R$_m$ is an initial radius and m' a factor needed to align the phases and offset the curvature of the paraboloid. If using the following approach:

$$m' = \frac{1}{1 + \frac{R_m}{\sqrt{F^2 + R_m^2}}}, \tag{7}$$

then the alignment of the phase of the wavefront will present an error of less than 1%. A more precise approach is possible, using series expansion to higher orders or by means of numerical techniques. The vertex of the helical-paraboloidal surface is at point r(θ,r,z)=(0,−¼a(θ),F), where:

$$\alpha(\theta) = \frac{r_c(\theta) - \sqrt{F^2 - 2Fz_c + r_c(\theta)^2 + z_c^2}}{2(F^2 - 2Fz_c + z_c^2)}. \tag{8}$$

In cylindrical coordinate representation r=r(θ,r,z), the surface of the reflector is defined as:

$$r(\theta, z) = \alpha(\theta)(z - F)^2 - \frac{1}{4\alpha(\theta)}, \tag{9}$$

where 0<θ<2π and 0<z<z$_{max}$, where z$_{max}$ is the height of the cylindrical electromagnetic generator. Since the position of the focus cannot be controlled electronically and is set by the focus of the helical-paraboloidal reflector, this implementation also requires a mechanical system for aligning the focal point (14) with the calculus to be fragmented.

Figure 7:
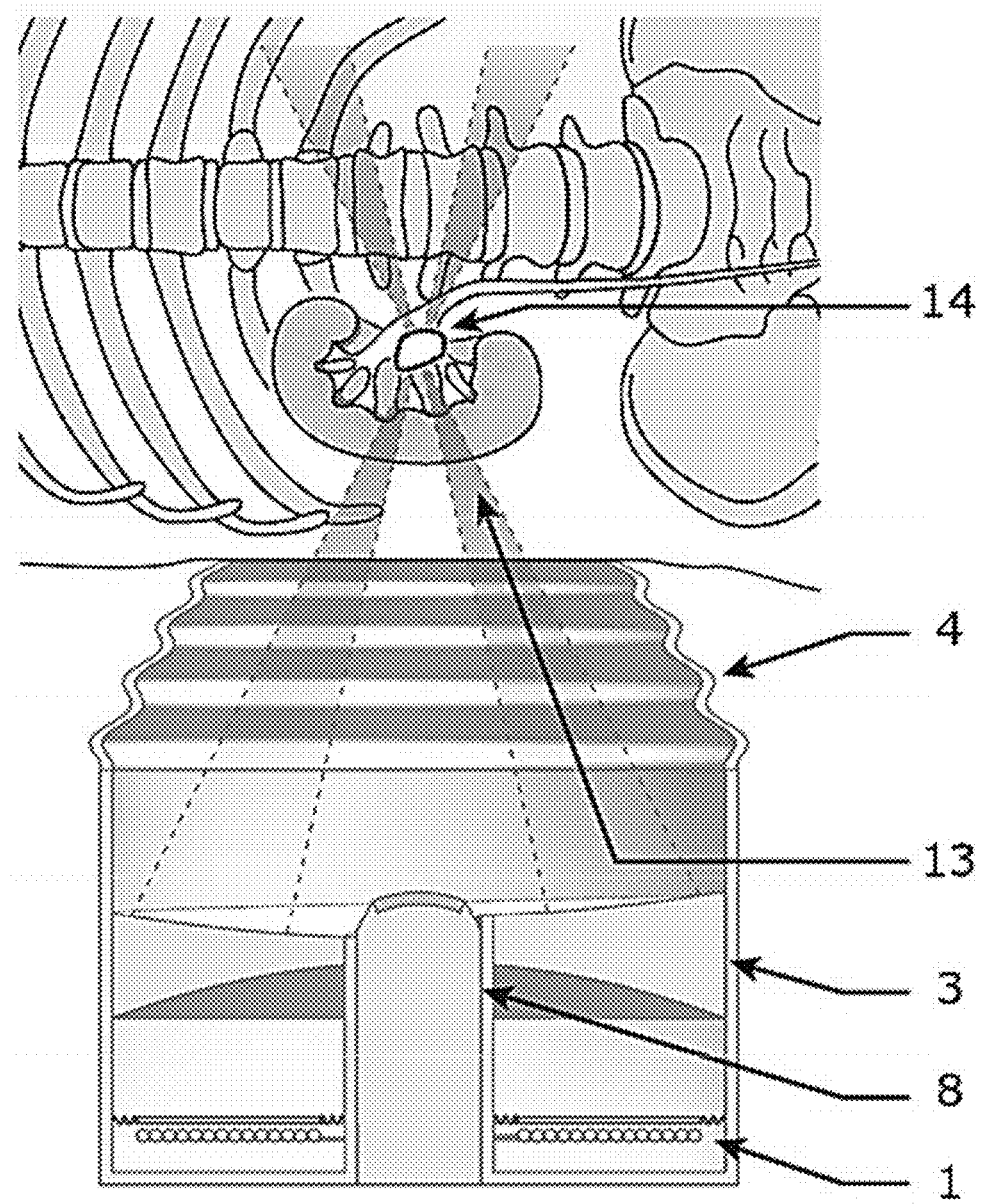
FIG. 7 shows an implementation of the system of the invention, whose vortex generator is of the electromagnetic type and includes a helical phase acoustic lens acting as the acoustic beam generation subsystem (3). The vortex beams (13) are oriented towards the focal point (14) of the system, which coincides with the position of the solid to be fragmented.
Figure 8:
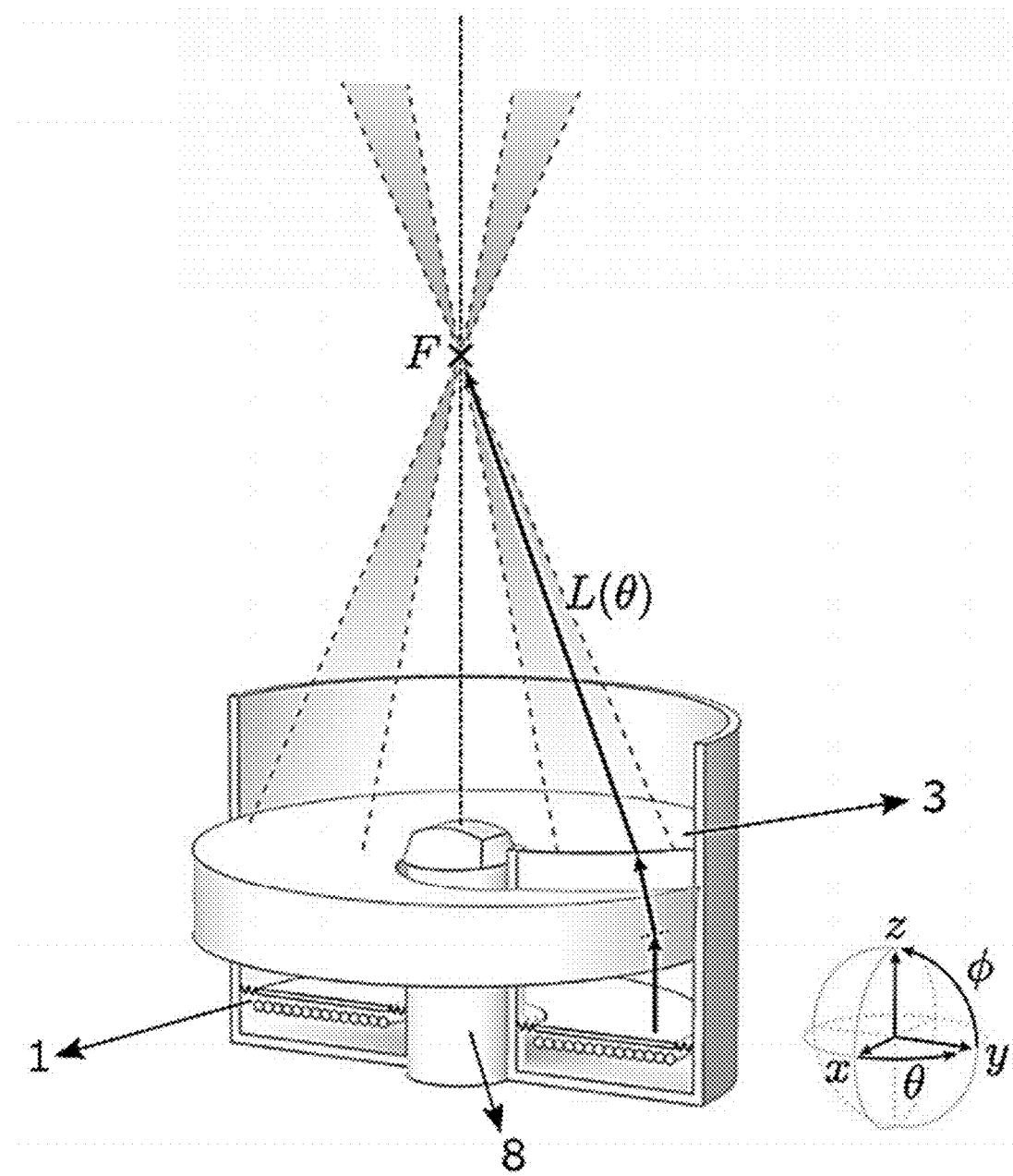
FIG. 8 includes a detailed diagram of the helical phase acoustic lens for the electromagnetic vortex generation system referred to in FIG. 7, which focuses on the focal point F.

In another preferred implementation, the generation of high-intensity vortexes comprises a first transduction subsystem (2) of the electromagnetic type with a flat surface and a circular or annular shape coupled to a helical phase lens, as illustrated in FIG. 7. The system uses a high-current electric pulse generation subsystem (1) for electrically exciting a coil adhered to a mobile, circular or annular surface, which on one of the faces thereof is in contact with a fluid. The induction of the coil generates a force which displaces the circular or annular surface in the axial direction in a transient manner. Said process produces a flat, transient, high pressure amplitude acoustic wavefront, which propagates along the fluid along the axial axis of the system. The system uses a helical phase lens to control the wavefront, which is generated in transmission (without the need for reflectors as in previous implementations) and is focused on a focal point (F) where the fragmentation of the calculi will take place. FIG. 8 details an acoustic lens model based on the refraction of acoustic waves when going through a medium the sound propagation speed of which is different from that experienced in the fluid. When the lens material has a propagation speed (c$_n$) greater than the propagation speed in the fluid (c$_0$), then the lens is double concave. This case occurs when the fluid is water and the lens material (e.g., metals, plastics or polymers) is solid. In the opposite case, when the lens material has a lower propagation speed than the fluid, the lens is double convex. The lens consists of a spherical surface on the first side and a helical-ellipsoidal surface on the second side. The design of the acoustic lens is detailed below. The helical-ellipsoidal surface can be defined in cylindrical coordinates by an elliptical profile of revolution the parameters of which vary as a function of the azimuthal angle θ. The eccentricity (ε) of such elliptical profiles is constant and is given by ε=c0/cn; while the focus of the profiles is given by:

$$c(\theta) = \left(F - \frac{m'M\lambda_0\theta}{2\pi}\right)\frac{1}{1 + 1/\varepsilon}, \tag{10}$$

wherein F is the geometric focus of the lens and m', in this case, has a value close to one and can be calculated numerically. Lastly, if it is taken into account that the major semi-axis of the helical-ellipsoidal surface is given by a(θ)=c(θ)/ε and the minor semi-axis is given by $$b(\theta) = c(\theta)\sqrt{\frac{1}{\varepsilon^2} - 1},$$

the surface of the helical-spheroidal lens is given by:

$$z(\theta, r) = m'M\frac{\theta}{2\pi} + \alpha(\theta)\left(1 - \sqrt{1 - \frac{r^2}{b(\theta)^2}}\right). \tag{11}$$

The other lens face, the spherical face, is given by the surface:

$$z(\theta,r) = -(R_c + \Delta z) + \sqrt{R_c^2 - r_2}, \tag{12}$$

wherein the radius of curvature is R$_c$=(F$_s$+Δz)(1−ε), where F$_s$ is the focal of the concave lens and Δz is the thickness thereof on the axial axis. The use of a spherical lens on the lower face is optional, but it reduces the limitations in the maximum aperture of the helical-ellipsoidal lens. For example, using a lens with a focal F$_s$=4F, the system makes it possible to produce large aperture vortex generators and thus higher acoustic intensities in the focal zone. Since the position of the focus cannot be electronically controlled and is set by the helical phase acoustic lens, a mechanical system is required to align the focal point (14) with the calculus.

Figure 9:
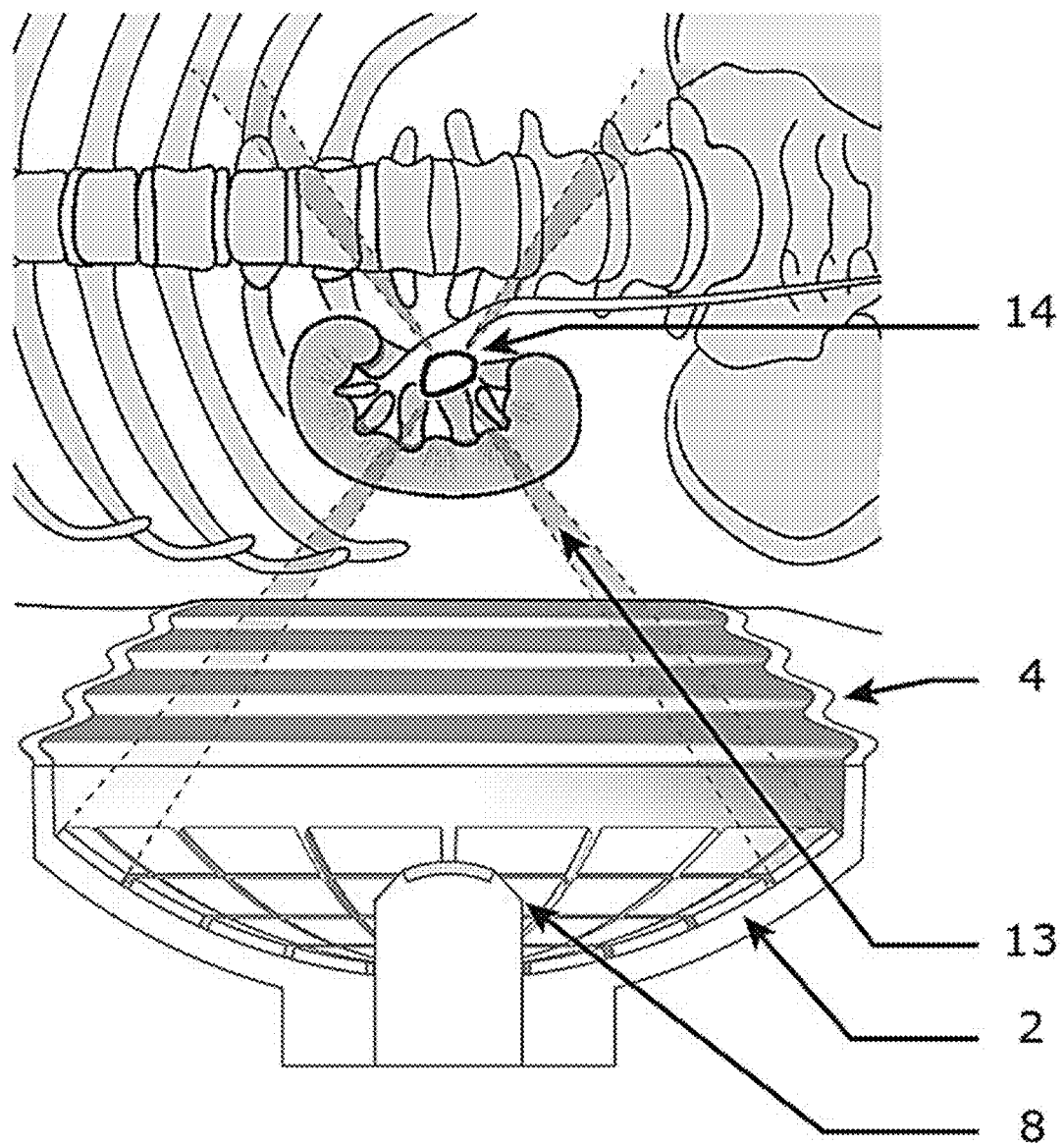
FIG. 9 illustrates a preferred implementation wherein the vortex generator comprises a multiple element piezoelectric transducer in phased array configuration as the electromechanical transduction subsystem (2). The vortex beams (13) are oriented towards the focal point (14) of the system, which coincides with the position of the solid to be fragmented.
Figure 10:
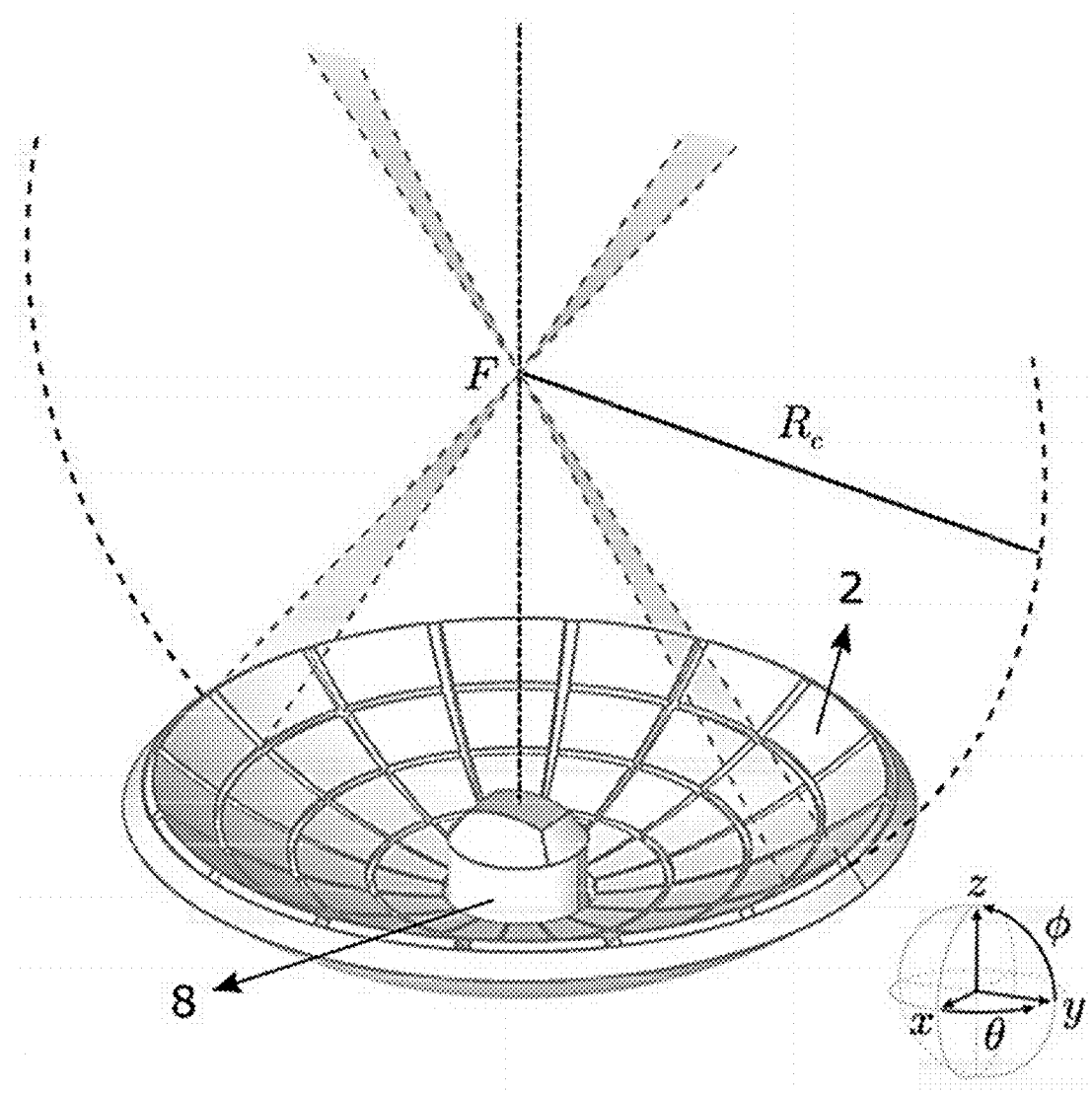
FIG. 10 shows a detailed diagram of the piezoelectric vortex generation system by means of the phased array referred to in FIG. 9.

In another preferred embodiment, the high-intensity acoustic beam generation subsystem (3) comprises a multiple element piezoelectric system configured as a phased array, as observed in FIG. 9. The system uses a multichannel high-voltage electric pulse generation subsystem (1) for electrically exciting a series of piezoelectric transducers arranged on a spherical surface and immersed in a fluid. Under the action of the transient electric field, the piezoelectric transducers constituting the first transduction subsystem (2) are deformed, compressing and expanding the fluid and generating a focused, transient, and high pressure amplitude acoustic wavefront, which converges towards the center of the spherical surface. The radius of the spherical surface coincides with the focal point (14) of the system where the fragmentation of the calculi will take place. The shape of the piezoelectric elements can be sectorial, circular, or hexagonal, among others; as well as their arrangement on the spherical surface, which preferably follows a regular pattern in polar coordinates or any other, periodic or not. Assuming that the piezoelectric elements of the phased array are equispaced in polar coordinates, to control the wavefront and generate the acoustic vortex a series of delays must be applied on each of the voltage pulses of the phased array shown in detail in FIG. 10. The value of each delay (τ) depends on the position θ of each piezoelectric element and is given by $\tau=(M\theta)/\omega_0$. This phased array thereby makes it possible to move the focal point F of the system, delaying each of the channels of the electronic excitation system until aligning the beams in phase. With this configuration, if the vortex is to be moved to point $r_F(x,y,z)=(F_x,F_y,F_z)$, the delays that must be applied to each of the elements of the phased array (which are centered around a point $r_0(x,y,z)$) are calculated as:

$$\Delta t(r_0, r_F) = \frac{\|r_F(x, y, z) - r_0(x, y, z)\|}{c_0} + r(\theta), \quad (13)$$

although for a phased array arranged on a spherical surface, the above expression is reduced to:

$$\Delta t(r_0, r_F) = \frac{1}{c_0}\sqrt{(x_0 - F_x)^2 + (y_0 - F_y)^2 + (z_0 - F_z)^2} + \frac{M}{\omega_0}\tan^{-1}\left(\frac{y}{x}\right). \quad (14)$$

The piezoelectric system allows the generation of long duration excitation signals, where the phase lags are given by a complex coefficient $\phi(r_0,r_F)=\exp(i\omega_0\Delta t)$, wherein the term $\omega_0\Delta t$ is used to delay sinusoidal signals or bursts when the excitation is not transient. This process allows the fragmentation of the calculi by striking with smaller amplitude beams, which mitigates the unwanted effects of treatment.

Figure 11:
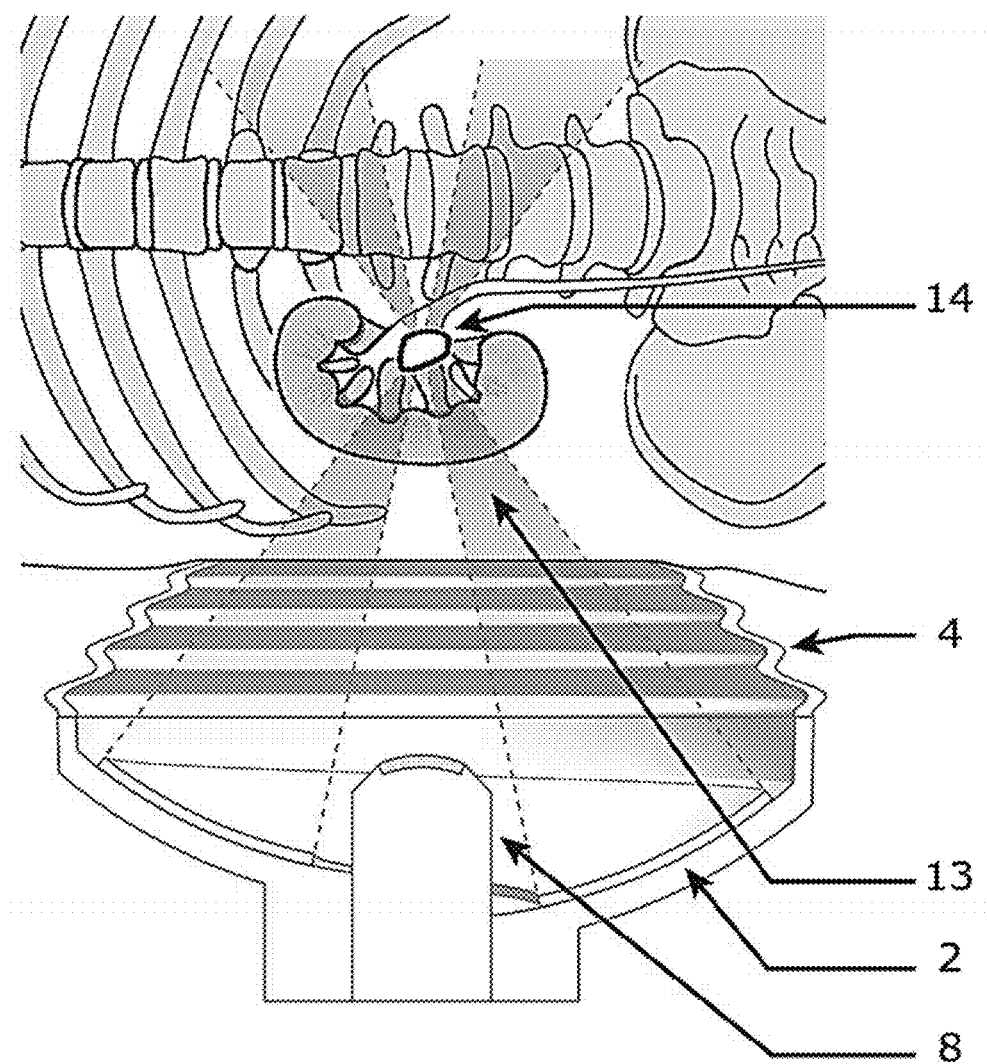
FIG. 11 shows a particular implementation wherein the electromechanical transduction subsystem (2) comprises a spherically focused single element piezoelectric helical-spheroidal transducer. The vortex beams (13) are oriented towards the focal point (14) of the system, which coincides with the position of the solid to be fragmented.
Figure 12:
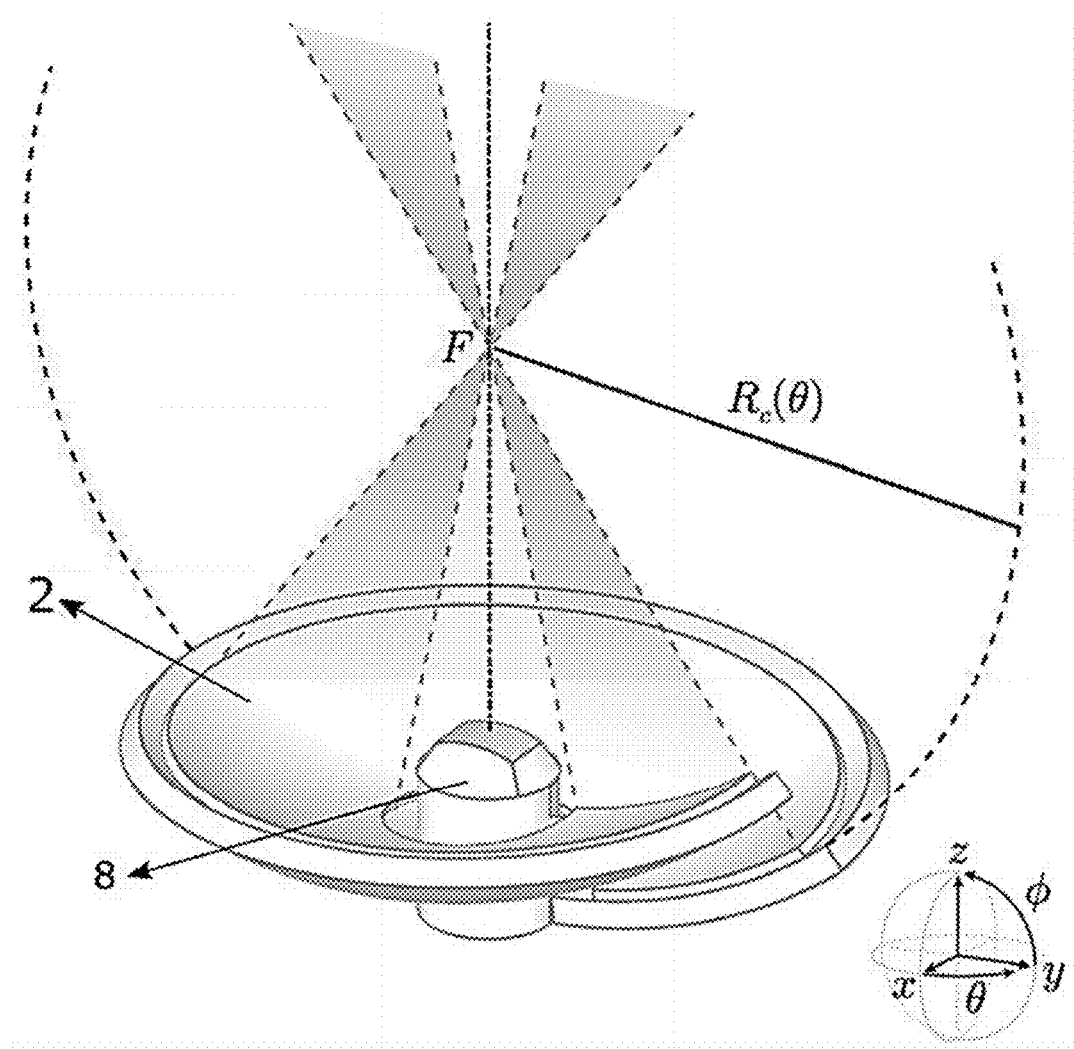
FIG. 12 shows a detailed diagram of the spherically focused single element piezoelectric helical-spheroidal transducer referred to in FIG. 11.
Figure 13:
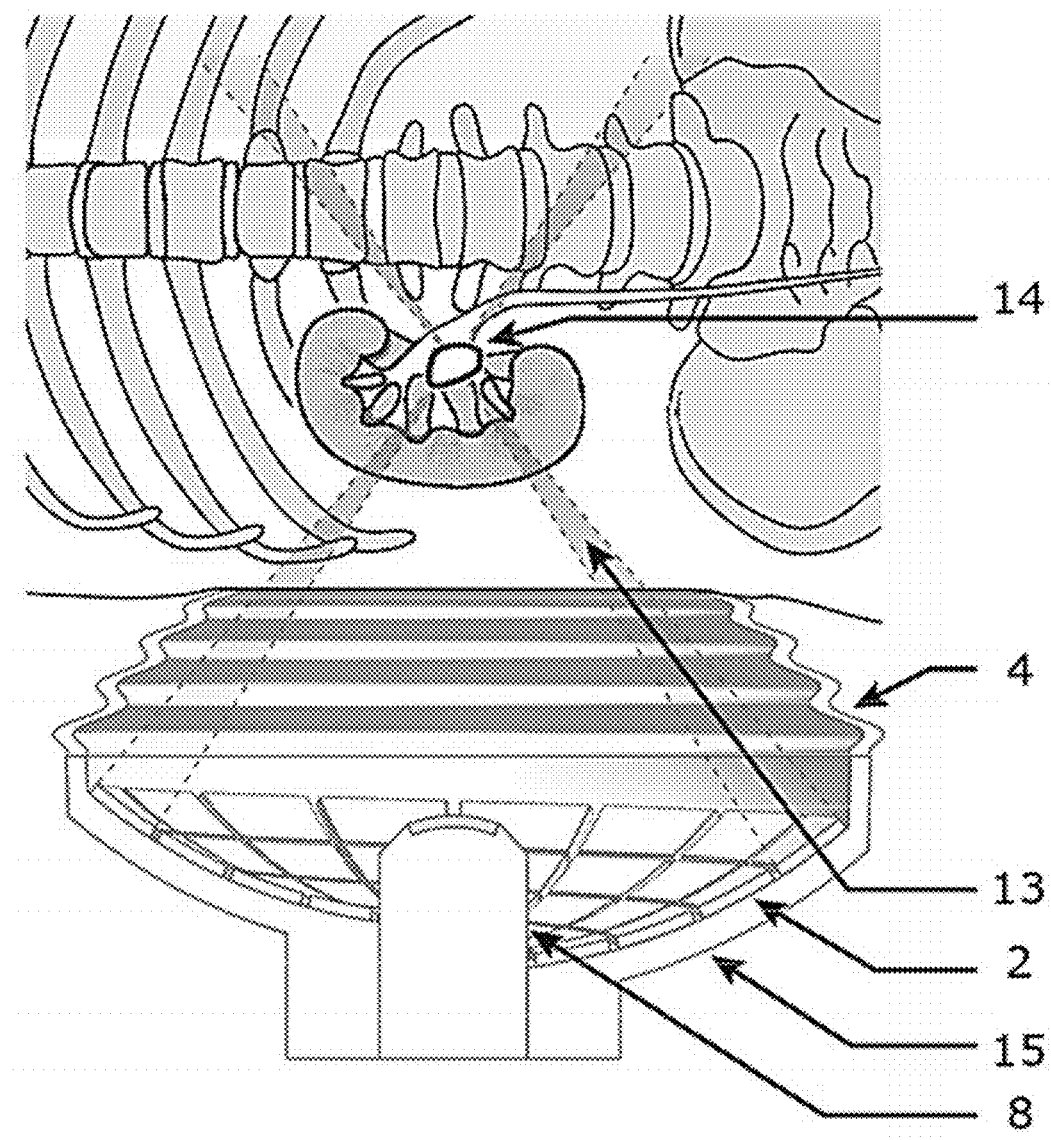
FIG. 13 illustrates a particular implementation wherein the transduction subsystem (2) of the electromechanical type is implemented by means of a spherically focused multiple element piezoelectric helical-spheroidal transducer. The vortex beams (13) are oriented towards the focal point (14) of the system, which coincides with the position of the solid to be fragmented.
Figure 14:
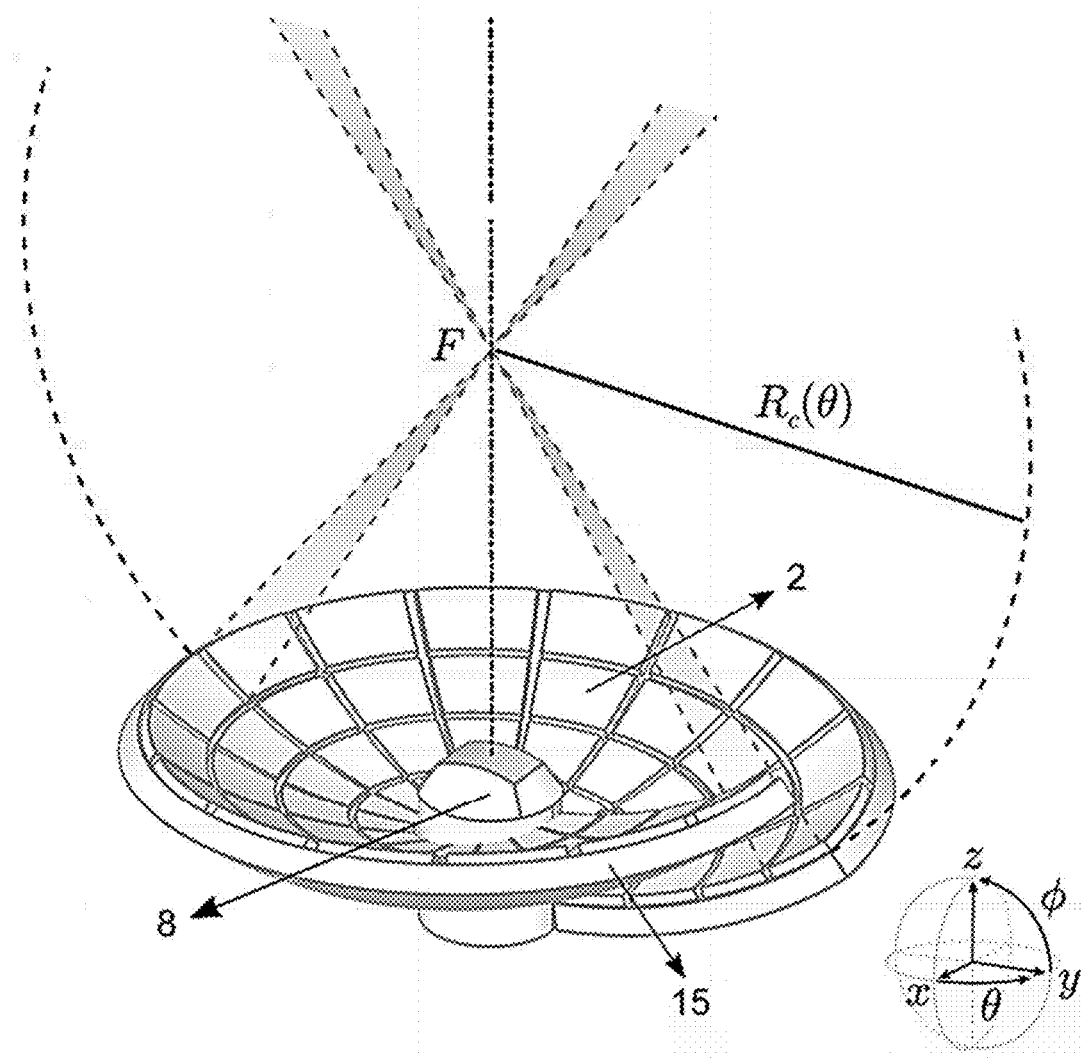
FIG. 14 shows a detailed diagram of the piezoelectric vortex generation system by means of a spherically focused multiple element arranged on a helical surface (15).

Another particularly advantageous realization is shown in FIG. 11, which is a variant of the system referred to in FIG. 9. Since the phased arrays require electronic control of the delays applied to each channel (which adds complexity to the design), the design in FIG. 11 uses a single high-voltage electric pulse generation subsystem (1) that excites a first transduction subsystem (2) consisting of a single piezoelectric transducer. The surface of the piezoelectric is helical-spheroidal, as illustrated in FIG. 12, and can be expressed as the azimuthal revolution of a circumferential arc section where the radius of curvature of the $$R_c(\theta) = F - \frac{M\lambda_0\theta}{2\pi}, \quad (15)$$

such that as a result of said curvature path difference is generated between the beams at the design frequency $\omega_0=2\pi c_0/\lambda_0$, which produces a vortex of topological charge M. For the design of the helical-spheroidal surface, its definition in spherical coordinates $r=r(\theta, \phi, r)$ is taken into account, which is given by $$x(\theta,\phi)=R_c(\theta)\cos(\theta)\sin(\phi), \quad (16)$$

$$\text{and } (\theta,\phi)=R_c(\theta)\sin(\theta)\sin(\phi), \quad (17)$$

$$z(\theta,\phi)=-F_2-R_c(\theta)\cos(\phi), \quad (18)$$

where $0<\theta<2\pi$ and the minimum and maximum limits of the angles of elevation are given by $\phi_{min}=\tan^{-1}(A_h/2F_2)$ and $\phi_{max}=\tan^{-1}(A/2F_2)$, where A is the transducer aperture and $A_h$ is the diameter of the lower gap of the transducer, which can be zero. The acoustic beam generation subsystem (3) of the piezoelectric type for generating acoustic beams by means of a single element transducer with a helical surface has a vortex at the focal point (14) whose position cannot be controlled, so that as with electrohydraulic and electromagnetic generators, a mechanical positioning subsystem (5) is required to align the focal point with the calculus to be fragmented, An even more advantageous embodiment of the invention comprises a first transduction subsystem (2) formed by multiple piezoelectric elements arranged on a helical surface, as shown in FIG. 13. In this way, the complications associated with the manufacture of a single piezoelectric transducer with a helical surface, as previously shown in FIGS. 11 and 12, are avoided. The multiple piezoelectric elements (transducers) depicted in FIG. 13 can be excited by a single electrical signal, which reduces the cost and complexity of the system compared to the phased array system of FIGS. 11-12. The acoustic beam generation subsystem (3) of the piezoelectric type for generating acoustic beams by means of a multiple element transducer with a helical surface has a vortex at the focal point (14) whose position cannot be controlled if the same signal is used for all the elements, so a mechanical positioning subsystem (5) is required to align the focal point (14) with the calculus. The detail of the curvature of the helical surface is shown in FIG. 14 and is described by Equations (15-18). The shape of the multiple piezoelectric elements can be sectorial, or any other (circular, hexagonal, etc.).

Additionally, another preferred embodiment of the invention comprises a first piezoelectric transduction subsystem (2) whose transducers may be single or multiple element transducers, and additionally comprises a helical-ellipsoidal phase acoustic lens for producing the focused vortices. The acoustic lens is placed over the piezoelectric transducer(s), each of which is excited with a pulsed or sinusoidal high voltage signal. The use of the acoustic lens allows the control of the beam focusing and, simultaneously, the generation of the vortex with arbitrary topological charge without the need to use a multichannel electronic device to excite each of the elements individually. Since the lens is a removable and easily interchangeable component of the system, several lenses can be interchanged to adjust the focal length, topological charge, design frequency and beam width and thus adjust the acoustic focus characteristics to the treatment to be performed. The lens design is given by Equations (10-12). In the case where the piezoelectric system is arranged on a flat circular surface, the lens will be flat on its lower face. Since the focal point (14) cannot be controlled electronically if the same signal is used for all piezoelectric elements or if a single piezoelectric element is used, and is set by the lens, a mechanical motion system is required to align the focal point with the calculus.

In the implementations in which the acoustic beam generation unit (100) involves electrohydraulic, electromagnetic, or piezoelectric transducers (whether it is a simple or multiple element transducer), the mechanical positioning subsystem (5) comprises at least one actuator which allows the focal point (14) of the system to be realigned.

Various preferred implementations of the feedback and control unit (200) are referred to below.

In a preferred implementation of the invention, the second electromechanical transduction subsystem (8) comprises a phased array of piezoelectric transducers to provide an ultrasonic imaging subsystem (9) in pulse echo modo.

In another even more advantageous implementation, the monitoring subsystem (10) of the treatment further comprises the means for recording the patient's natural movements (for example, breathing) in real time and comprises at least one movement sensor. The recorded data are used by the control subsystem (7) to automatically correct the misalignment of the focal point (14) of the system due to the (voluntary or involuntary) movement of the patient.

In some alternative embodiments of the invention, the feedback and control unit (200) can be dispensed with. Such solutions are considered suboptimal because they would not allow the monitoring and modulation of the ultrasonic treatment in a continuous manner; and they would also require applying a predefined sequence of electric pulses to later interrupt treatment and acquire some type of image (by X-rays, ultrasounds, etc.) to allow the results thereof to be evaluated.

The invention claimed is:

1. A system for the controlled fragmentation of solids with acoustic beams, comprising at least:
   one acoustic beam generation unit which, in turn, comprises:
      an electric pulse generation subsystem;
      a first transduction subsystem, adapted for converting electric pulses into acoustic waves;
      an acoustic beam generation subsystem for generating acoustic beams from the acoustic waves produced by the transduction subsystem and for focusing said beams in a focal volume in which a solid or solids to be fragmented are located;
      an acoustic coupling subsystem, adapted for coupling the acoustic beams to the solid or solids to be fragmented;
      a positioning subsystem, adapted for adjusting the position of the focal point;
   one feedback and control unit comprising:
      a control subsystem, which controls the acoustic beam generation unit;
      a second transduction subsystem, adapted for the acquisition of information relating to the acoustic beams;
      a processing subsystem for processing the information acquired by the second transduction subsystem;
   wherein:
      the acoustic beams are acoustic vortex beams;
      the feedback and control unit further comprises a feedback subsystem, configured to receive the information processed by the processing subsystem and send the information to the control subsystem; and
      the control subsystem is configured to modify, based on the information sent by the feedback subsystem, parameters of the acoustic vortex beams, wherein said parameters comprise the topological charge of the acoustic vortex beams.

2. The system according to claim 1, wherein the acoustic vortex beams are ultrasonic acoustic vortex beams.

3. The system according to claim 1, wherein the feedback and control unit comprises a pulse echo ultrasonic imaging subsystem and further comprises a monitoring subsystem for monitoring the solid or solids equipped for the graphical representation of information associated with said solid or solids.

4. The system according to claim 1, wherein the information processing subsystem comprises real-time measurement of the cavitation produced substantially at the focal point of the system, and wherein the feedback subsystem is further configured to process said information and readjust the acoustic beams striking the mentioned focal point.

5. The system according to claim 1, wherein the first transduction subsystem is of the electrohydraulic type, and wherein the acoustic beam generation subsystem comprises a reflector with a helical-ellipsoidal surface for generating the vortex in reflection; and wherein the positioning subsystem is furthermore of the mechanical type for aligning the focal point of the system with the solid to be fragmented.

6. The system according to claim 1, wherein the first transduction subsystem is of the electromagnetic type and wherein the acoustic beam generation subsystem comprises a helical-paraboloidal reflector; and wherein the positioning subsystem is furthermore of the mechanical type for aligning the focal point of the system with the solid to be fragmented.

7. The system according to claim 1, wherein the first transduction subsystem is of the electromagnetic type and wherein the acoustic beam generation subsystem comprises an acoustic lens.

8. The system according to claim 7, wherein the acoustic lens furthermore has a helical or helical-ellipsoidal phase profile.

9. The system according to claim 1, wherein the first transduction subsystem is of the piezoelectric type and wherein the acoustic beam generation subsystem comprises a multiple element phased array immersed in a fluid; and wherein the positioning subsystem is of the electronic type and configures the delays applied to the excitation signal of each of a plurality of channels of the phased array for readjusting the position of the focal point of the system.

10. The system according to claim 1, wherein the first transduction subsystem comprises a single piezoelectric transducer immersed in a fluid, with the arrangement of said transducer on a helical-spheroidal surface being what provides the acoustic beam generation subsystem; and wherein the system further comprises the positioning subsystem of the mechanical type for adjusting the focal point of the system.

11. The system according to claim 1, wherein the first transduction subsystem comprises a multiple element piezoelectric transducer immersed in a fluid, with the arrangement of each of a plurality of channels thereof on a helical-spheroidal surface being what provides the acoustic beam generation subsystem; said system further comprising the positioning subsystem of the mechanical type for adjusting the focal point of the system.

12. The system according to claim 1, wherein the first transduction subsystem is of the piezoelectric type and wherein the acoustic beam generation subsystem comprises an acoustic lens.

13. The system according to claim 12, wherein the acoustic lens has a helical or helical-ellipsoidal phase profile.

14. The system according to claim 1, for use in lithotripsy.

15. The system according to claim 14, wherein the feedback and control unit comprises a plurality of actuators for readjusting the focal point of said system.

* * * * *